US006485910B1

(12) United States Patent
Walker et al.

(10) Patent No.: US 6,485,910 B1
(45) Date of Patent: Nov. 26, 2002

(54) RAS ASSOCIATION DOMAIN CONTAINING PROTEIN

(75) Inventors: Michael G. Walker, Sunnyvale, CA (US); Tod M. Klinger, San Carlos, CA (US); Randi E. Krasnow, Stanford, CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 10 days.

(21) Appl. No.: 09/614,069

(22) Filed: Jul. 11, 2000

Related U.S. Application Data

(63) Continuation-in-part of application No. 09/195,292, filed on Nov. 18, 1998, now abandoned, and a continuation-in-part of application No. 09/023,655, filed on Feb. 9, 1998.

(51) Int. Cl.$^7$ ................................................ C12Q 1/68
(52) U.S. Cl. .............................. 435/6; 435/6; 435/69.1; 435/91.1; 435/91.2; 536/23.1; 536/24.1; 530/350
(58) Field of Search .......................... 435/6, 91.1, 91.2, 435/69.1; 536/23.1, 24.1; 530/350

(56) References Cited

PUBLICATIONS

Slepnev et al. National Center for Biotechnology Information. National Library of Medicine, National Insitutes of Health, Bethesda, MD. Accession No. AF002251. Rattus norvegicus mRNA, complete cds.*
Fantl, W.J. et al.; "Signalling By Receptor Tyrosine Kinases"; Annu Rev Biochem 62:453–481 (1993).
Woodrow, M.A. et al.; "p21$^{ras}$ Function Is Important for T Cell Antigen Receptor and Protein Kinase C Regulation of Nuclear Factor of Activated T Cells"; J Immunol 150(9):3853–3861 (May 1, 1993).
van Corven, E.J. et al.; "Pertussis toxin–sensitive activation of p21$^{ras}$ by G protein–coupled receptor agonists in fibroblasts"; Proc Natl Acad Sci 90:1257–1261 (Feb. 1993).
Avruch, J. et al.; "Raf meets Ras: completing the framework of a signal transduction pathway"; Trends Biochem Sci 19:279–283 (1994).
Barbacid, M.; "ras Genes"; Annu Rev Biochem 56:779–827 (1987).
Treisman, R.; "Ternary complex factors: growth factor regulated transcriptional activators"; Curr Opin Genet Dev 4:96–101 (1994).
Bos, J.L.; "ras Oncogenes in Human Cancer: A Review"; Cancer Res 49;4682–4689 (Sept. 1, 1989).

Grunicke, H.H. and Maly, K.; "Role of GTPases and GTPase Regulatory Proteins in Oncogenesis"; Critical Rev in Oncogenesis 4(4):389–402 (1993).
Katz, M.E. and McCormick, F.; "Signal transduction from multiple Ras effectors"; Curr Opin Genet Dev 7:75–79 (1997).
Albright, C.F. et al.; "Characterization of a quanine nucleotide dissociation stimulator for a ras–related GTPase"; EMBO J 12(1):339–347 (1993).
Kikuchi, A. and Williams, L.T.; "Regulation of Interaction of ras p21 with RalGDS and Raf–1 by Cyclic AMP–dependent Protein Kinase", J Biol Chem 271(1):588–594 (1996).
Urano, T. et al.; "Ral–GTPases mediate a distinct downstream signaling pathway from Ras that facilitates cellular tranformation"; EMBO J 15(4):810–816 (1996).
Gai, T. et al.; "An EGF receptor/Ral–GTPase signaling cascade regulates c–Src activity and substrate specificity"; EMBO J 19(4):623–630 (2000).
Feig, L.A. et al.; "Evidence for a Ras/Ral signaling cascade"; Trends Biochem 21:438–41 (Nov. 1996).
Voss, M. et al.; "Phospholipase D Stimulation by Receptor Tytrosine Kinases Mediated by Protein Kinase C and a Ras/Ral Signaling Cascade"; J Biol Chem 274(49):34691–34698 (1999).
Vavvas, D. et al.; "Identification of Norel as a Potential Ras Effector"; J Biol Chem 273(10):5439–5442 (1998).
Pazdrak, K. et al.; "The Intracellular Signal Transduction Mechanism of Interleukin 5 in Eosinophils: The Involvement of Lyn Tyrosine Kinase and the Ras–Raf–1–MEK–Microtubule–associated Protein Kinase Pathway"; J Exp Med 181:1827–1834 (May 1995).
Adachi, T. and Alam, R.; "The mechanism of IL–5 signal transduction"; Am J Physiol 275 (Cell Physiol 44):C623–633 (1998).
M'Rabet, L. et al.; "Differential fMet–Leu–Phe– and Platelet–activating Factor–induced Signaling Toward Ral Activation in Primary Human Neutrophils"; J Biol Chem 274(31):21847–21852 (1999).

* cited by examiner

Primary Examiner—W. Gary Jones
Assistant Examiner—Janell E. Taylor
(74) Attorney, Agent, or Firm—Incyte Genomics, Inc.

(57) ABSTRACT

The invention provides a mammalian cDNA which encodes a mammalian Ras association domain containing protein. It also provides for the use of the cDNA, fragments, complements, and variants thereof and of the encoded protein, portions thereof and antibodies thereto for diagnosis and treatment of cell proliferative and inflammatory disorders, particularly thymus hyperplasia, allergies, asthma, and hypereosinophilia. The invention additionally provides expression vectors and host cells for the production of the protein and a transgenic model system.

14 Claims, 11 Drawing Sheets

5' TTG ATG CGC TGG CGG CCT CGG CCG GGA ACT CCG GGG TAG ATG ACC GTG GAC AGC
                11          20          29          38          47          56
                                                                M   T   V   D   S

AGC ATG AGC AGT GGG TAC TGC AGC TTC AGA CTG GAC GAG GAA CTG GAA GAC TGC TTC TTC
        65          74          83          92          101         110
    S   M   S   S   G   Y   C   S   F   R   L   D   E   E   L   E   D   C   F   F

ACT GCT AAG ACT ACC TTT TTC AGA AAT GCG CAG AGC AAA CAT CTT TCA AAG AAT
        119         128         137         146         155         164
    T   A   K   T   T   F   F   R   N   A   Q   S   K   H   L   S   K   N

GTC TGT AAA CCT GTG GAG GAG ACA CAG CGC CCG CCC ACA CTG CAG GAG ATC AAG
        173         182         191         200         209         218
    V   C   K   P   V   E   E   T   Q   R   P   P   T   L   Q   E   I   K

CAG AAG ATC GAC AGC TAC AAC ACG CGA GAG AAG AAC TGC CTG GGC ATG AAA CTG
        227         236         245         254         263         272
    Q   K   I   D   S   Y   N   T   R   E   K   N   C   L   G   M   K   L

FIGURE 1A

```
       281            290            299            308            317            326
AGT GAA GAC GGC ACC TAC ACG GGT TTC ATC AAA GTG CAT CTG AAA CTC CGG CGG
 S   E   D   G   T   Y   T   G   F   I   K   V   H   L   K   L   R   R 335            344            353            362            371            380
CCT GTG ACG GTG CCT GCT GGG CCC CAG TCC ATC TAT GAT GCC ATC AAG
 P   V   T   V   P   A   G   P   Q   S   I   Y   D   A   I   K 389            398            407            416            425            434
GAG GTG AAC CTG GCG GCT ACC ACG AAG CGG GAC ACA TCC TTC TAC CTG CCC CTA
 E   V   N   L   A   A   T   T   K   R   D   T   S   F   Y   L   P   L 443            452            461            470            479            488
GAT GCC ATC AAG CAG CTG CAC ATC AGC ACC AGC ACC ACC GTC AGT GAG GTC ATC
 D   A   I   K   Q   L   H   I   S   T   S   T   T   V   S   E   V   I 497            506            515            524            533            542
CAG GGG CTG CTC AAG TTC ATG GTT GTG GAC AAT CCC CAG AAG TTT GCA CTT
 Q   G   L   L   K   F   M   V   V   D   N   P   Q   K   F   A   L
```

FIGURE 1B

FIGURE 1C

```
551            560            569            578            587            596
TTT AAG CGG ATA CAC AAG GAC GGA CAA GTG CTC TTC CAG AAA CTC TCC ATT GCT
 F   K   R   I   H   K   D   G   Q   V   L   F   Q   K   L   S   I   A 605            614            623            632            641            650
GAC CGC CCC CTC TAC CTG CGC CTT GCT GGG CCT GAC ACG GAG GTC CTC AAC
 D   R   P   L   Y   L   R   L   A   G   P   D   T   E   V   L   N 659            668            677            686            695            704
CTA AAG GAG AAT GAA ACT GGA GAG GTA GAG TGG GAT GCC TTC ATC
 L   K   E   N   E   T   G   E   V   E   W   D   A   F   I 713            722            731            740            749            758
CTT CAG AAC TTC CTA ACA ATC CTG GAA AAA GAG GAG CAG GAC AAA ATC
 F   V   Q   N   F   L   T   I   L   E   K   E   E   Q   D   K   I 767            776            785            794            803            812
CAA GTG CAA AAG TAT GAC AAG TTT AGG CAG AAA CTG GAG GAG GCC TTA
 Q   Q   V   Q   K   Y   D   K   F   R   Q   K   L   E   E   A   L
```

```
     821         830         839         848         857         866
AGA GAA TCC CAG GGC AAA CCT GGG TAA CCG GTC CTG CTT CCT CTC CTG GTG
 R   E   S   Q   G   K   P   G   -
     875         884         893         902         911         920
CAT TCA GAT TTA TTT GTA TTA TTT ATT ATT ATT TTG CAA CAG ACA CTT TTT CTC
     929         938         947         956         965         974
AGG ACA TCT CTG GCA GGT GCA TTT GTG CCT GCC CAG CAG TTC CAG CTG TGG CAA
     983         992        1001        1010        1019        1028
AAG TCT CTT CCA TGG ACA AGT GTT TGC ACG GGG GTT CAG CTG TGC CCG CCC CCA
    1037        1046        1055        1064        1073        1082
GGC TGT GCC CCA CCA CAG ATT CTG CCA AGG ATC AGA ACT CAT GTG AAA CAA ACA
    1091        1100        1109        1118        1127        1136
GCT GAC GTC CTC TCT CGA TCT GCA AGC CTT TCA CCA ACC AAA TAG TTG CCT CTC
    1145        1154        1163        1172        1181        1190
TCG TCA CCA AAC TGG AAC CTC ACA CCA GCC GGC AAA GGA AGG AAG AAA GGT TTT
    1199        1208        1217        1226        1235        1244
AGA GCT GTG TGT TCT TTC TCT GGC TTT GAT TCT TCT TTG AGT TCT CTT ACT TGC
    1253        1262        1271        1280        1289        1298
CAC GTA CAG GAC CAT TAT TTA TGA GTG AAA AGT TGT AGC ACA TTC CTT TTG CAG
```

FIGURE 1D

```
          1307            1316            1325            1334            1343            1352
GTC TGA GCT AAG CCC TTG AAA GCA GGG TAA TGC TCA TAA AAG GAC TGT TCC CGC
          1361            1370            1379            1388            1397            1406
GGC CCC AAG GTG CCT GTT GTT CAC ACT TAA GGG AAG TTT ATA AAG CTA CTG GCC
          1415            1424            1433            1442            1451            1460
CCA GAT GCT CAG GGT AAG GAG CAC CAA AGC TGA GGC CTC AGA GAT CTC CAG
          1469            1478            1487            1496            1505            1514
AGA AGC TGC AGC CTG CCC TGG CTC TGG CCC TGG CCC ACA TTG CAC ATG
          1523            1532            1541            1550            1559            1568
GAA ACC CAA AGG CAT ATA TCT GCG TAT GTG TGG TAC TTA GTC ACA TCT TTG TCA
          1577            1586            1595            1604            1613            1622
ACA AAC TGT TCG TTT TTA AGT TAC AAA TTT GAA TTT AAT GTT GTC ATC ATC GTC
          1631            1640            1649            1658            1667            1676
ATG TGT TTC CCC AAA GGG AAG CCA GTC ATT GAC CAT TTA AAA AGT CTC CTG CTA
          1685            1694            1703            1712            1721            1730
AGT ATG GAA ATC AGA CAG TAA GCC AAA AAG CAA TGC AGA GAA AGG TGT
          1739            1748            1757            1766            1775            1784
CCA AGC TGT CTT CAG CCT TCC CCA GCT AAA GAG CAG AGG AGG TGG GCT ACT
```

FIGURE 1E

```
      1793         1802         1811         1820         1829         1838
TGG GTT CCC CAT CGG CCT CCA GCA CTG CCT CCC TCC CAC TGC GAC TCT GGG 1847         1856         1865         1874         1883         1892
ATC TCC AGG TGC TGC CCA AGG AGT TGC CTT GAT TAC AGA GAG GGG AGC CTC CAA 1901         1910         1919         1928         1937         1946
TTC GGC CAA CTT GGA GTC CTT TCT GTT TTG AAG CAT GGG CCA GAC CCG GCA CTG 1955         1964         1973         1982         1991         2000
CGC TCG GAG AGC CGG TGG GCC TGG CCT CGA CCT CAG TGC CTT TTT GTT 2009         2018         2027         2036         2045         2054
TTC AGA GAG AAA TAG GAG TAG GGC GAG TTT GCC TGA AGC TCT GCT GGC TTC 2063         2072         2081         2090         2099         2108
TCC TGC CAG GAA GTG AAC AAT GGC GGC GGT GTG GGA GAC AAG GCC AGG AGA GCC 2117         2126         2135         2144         2153         2162
CGC GTT CAG TAT GGG TTG AGG GTC ACA GAC CTC CCT CCC ATC TGG GTG CCT GAG 2171         2180         2189         2198         2207         2216
TTT TGA CTC CAA TCA GTG ATA CCA GAC CAC ATT GAC AGG GAG GAT CAA ATT CCT 2225         2234         2243         2252         2261         2270
GAC TTA CAT TTG CAC TGG CTT CTT TAG GCT GAA TCC TAA AAT AAA TTA GTC
```

FIGURE 1F

```
         2279      2288      2297      2306      2315      2324
AAA AAA TTC CAA CAA GTA GCC AGG ACT GCA GAG ACA CTC CAG TGC AGA GGG AGA
    2333      2342      2351      2360      2369      2378
AGG ACT TGT AAT TTT CAA AGC AGG GCT GGT TTT CCA ACC CAG CCT CTG AGA AAC
    2387      2396      2405      2414      2423      2432
CAT TTC TTT GCT ATC CTC TGC CTT CCC AAG TCC CTC TTG GGT CGG TTC AAG CCC
    2441      2450      2459      2468      2477      2486
AAG CTT GTT CGT GTA GCT TCA GAA GTT CCC TCT CCG ACC CAG GCT GAG TCC ATA
    2495      2504      2513      2522      2531      2540
CTG CCC CTG ATC CCA GAA GGA ATG CTG ACC CCT CGT ATG AAC TGT GCA TAG
    2549      2558      2567      2576      2585      2594
TCT CCA GAG CTT CAA AGG CAA CAC AAG CTC GCA ACT CTA AGA TTT TTT TAA ACC
    2603      2612      2621      2630      2639      2648
ACA AAA ACC CTG GTT AGC CAT CTC ATG CTC AGC CTT ATC ACT TCC CCT TTA
    2657      2666      2675      2684      2693      2702
GAA ACT CTC TCC CTG CTG TAT ATT AAA GGG AGC AGG TGG AGA GTC ATT TTC CTT
    2711      2720      2729      2738      2747      2756
CGT CCT GCA TGT CTC TAA CAT TAA CAT TAA TAG AAG GCA TGG CTC CTG CAA CCG CTG
```

FIGURE 1G

```
                2765            2774            2783            2792            2801            2810
         TGA ATG CTG AGA ACC TCC CTC TAT GGG GAT GGC TAT TTT ATT TTT GAG AAG
                2819            2828            2837            2846            2855            2864
         GAA AAA AGT CAT GTA TAT ATA CAC ATA AAG GCA TAT AGC TAT ATA TAA AGA
                2873            2882            2891            2900            2909            2918
         GAT AAG GGT GTT TAT GAA ATG AGA AAA TTA TTG GAC AAT TCA GAC TTT ACT AAA
                2927            2936            2945            2954            2963            2972
         GCA CAG TTA GAC CCA AGG CCT ATG CTG AGG TCT AAA CCT CTG AAA AAA GTA TAG
                2981            2990            2999            3008            3017            3026
         TAT CGA GTA CCC GTT CCC TCC CAG AGG TGG GAG TAA CTG CTG GTA GTG CCT TCT
                3035            3044            3053            3062            3071            3080
         TTG GTT GTG TTG CTC AGT GTG TAA GTG TTT GTT TCC AGG ATA TTT TCT TTT TAA
                3089            3098            3107            3116            3125            3134
         ATG TCT TTC TTA TAT GGG TTT TAA AAA AAA GTA ATA AAA GCC TGT TGC AAA AAT
         3143
         GAA AAA AAA A 3'
```

| | | |
|---|---|---|
| 39 | - - - - - S K N V C K P V E E T Q R P P T L Q E I K Q K I | 2726173 |
| 181 | T L T P T F N K V C K A V E E T Q H P P T I Q E I K Q K I | g2459833 |
| 181 | T L T P T L N Q N V C K A V E E T Q H P P T I Q E I K Q K I | g2997698 |
| | | |
| 63 | D S Y N T R E K N C L G M K L S E D G T Y T G F I K V H L K | 2726173 |
| 211 | D S Y N S R E K H C L G M K L S E D G T Y T G F I K V H L K | g2459833 |
| 211 | D S Y N S R E K H C L G M K L S E D G T Y T G F I K V H L K | g2997698 |
| | | |
| 93 | L R R P V T V P A G I R P Q S I Y D A I K E V N L A A T T D | 2726173 |
| 241 | L R R P V T V P A G I R P Q S I Y D A I K E V N P A A T T D | g2459833 |
| 241 | L R R P V T V P A G S G P S P S M D A I K E V N P A A T T D | g2997698 |
| | | |
| 123 | K R T S F Y L P L D A I K Q L H I S S T T T V S E V I Q G L | 2726173 |
| 271 | K R T S F Y L P L D A I K Q L H I S S T T T V S E V I Q G L | g2459833 |
| 271 | K R T S F Y L P L D A I K Q L H I S S T T T V S E V I Q G L | g2997698 |
| | | |
| 153 | L K K F M V V D N P Q K F A L F K R I H K D G Q V L F Q K L | 2726173 |
| 301 | L K K F M V V D N P Q K F A L F K R I H K D G Q V L F Q K L | g2459833 |
| 301 | L K K F M V V D N P Q K F A L F K R I H K D G Q V L F Q K L | g2997698 |

Figure 2B

| | | |
|---|---|---|
| 183 | SIADRPLYLRLLAGPDTEVLNFVLKENETG | 2726173 |
| 331 | SIADCPLYLRLLAGPDTDVLSFVLKENETG | g2459833 |
| 331 | SIADYPLYLRLLAGPDTDVLSFVLKENETG | g2997698 |

| | | |
|---|---|---|
| 213 | EVEWDAFSIPELQNFLTILEKEEQDKIQQV | 2726173 |
| 361 | DVEWDAFSIPELQNFLTILEKEEQDKIHQL | g2459833 |
| 361 | EVEWDAFSIPELQNFLTILEKEEQDKIHQL | g2997698 |

| | | |
|---|---|---|
| 243 | QKKYDKFRQKLEEALRESQGKPG | 2726173 |
| 391 | QKKYNKFRQKLEEALRESQGKPG | g2459833 |
| 391 | QKKYNKFRQKLEEALRESQGKPG | g2997698 |

Figure 2C

SEQUENCE LISTING

```
<160> NUMBER OF SEQ ID NOS:    14

<210> SEQ ID NO 1
<211> LENGTH: 265
<212> TYPE: PRT
<213> ORGANISM: Homo sapiens
<220> FEATURE:
<221> NAME/KEY: misc_feature
<223> OTHER INFORMATION: Incyte ID No: 2726173CD1

<400> SEQUENCE: 1

Met Thr Val Asp Ser Ser Met Ser Ser Gly Tyr Cys Ser Leu Asp
 1               5                  10                  15

Glu Glu Leu Glu Asp Cys Phe Phe Thr Ala Lys Thr Thr Phe Phe
                20                  25                  30

Arg Asn Ala Gln Ser Lys His Leu Ser Lys Asn Val Cys Lys Pro
                35                  40                  45

Val Glu Glu Thr Gln Arg Pro Pro Thr Leu Gln Glu Ile Lys Gln
                50                  55                  60

Lys Ile Asp Ser Tyr Asn Thr Arg Glu Lys Asn Cys Leu Gly Met
                65                  70                  75

Lys Leu Ser Glu Asp Gly Thr Tyr Thr Gly Phe Ile Lys Val His
                80                  85                  90

Leu Lys Leu Arg Arg Pro Val Thr Val Pro Ala Gly Ile Arg Pro
                95                  100                 105

Gln Ser Ile Tyr Asp Ala Ile Lys Glu Val Asn Leu Ala Ala Thr
                110                 115                 120

Thr Asp Lys Arg Thr Ser Phe Tyr Leu Pro Leu Asp Ala Ile Lys
                125                 130                 135

Gln Leu His Ile Ser Ser Thr Thr Thr Val Ser Glu Val Ile Gln
                140                 145                 150

Gly Leu Leu Lys Lys Phe Met Val Val Asp Asn Pro Gln Lys Phe
                155                 160                 165
```

```
Ala Leu Phe Lys Arg Ile His Lys Asp Gly Gln Val Leu Phe Gln
            170                 175                 180

Lys Leu Ser Ile Ala Asp Arg Pro Leu Tyr Leu Arg Leu Leu Ala
            185                 190                 195

Gly Pro Asp Thr Glu Val Leu Asn Phe Val Leu Lys Glu Asn Glu
            200                 205                 210

Thr Gly Glu Val Glu Trp Asp Ala Phe Ser Ile Pro Glu Leu Gln
            215                 220                 225

Asn Phe Leu Thr Ile Leu Glu Lys Glu Gln Asp Lys Ile Gln
            230                 235                 240

Gln Val Gln Lys Lys Tyr Asp Lys Phe Arg Gln Lys Leu Glu Glu
            245                 250                 255

Ala Leu Arg Glu Ser Gln Gly Lys Pro Gly
            260                 265

<210> SEQ ID NO 2
<211> LENGTH: 3144
<212> TYPE: DNA
<213> ORGANISM: Homo sapiens
<220> FEATURE:
<221> NAME/KEY: misc_feature
<223> OTHER INFORMATION: Incyte ID No: 2726173CB1

<400> SEQUENCE: 2
ccttgatgcg ctggcggcct cggccgggaa ctccggggta gatgaccgtg gacagcagca      60
tgagcagtgg gtactgcagc ctggacgagg aactggaaga ctgcttcttc actgctaaga    120
ctaccttttt cagaaatgcg cagagcaaac atctttcaaa gaatgtctgt aaacctgtgg    180
aggagacaca gcgcccgccc acactgcagg agatcaagca gaagatcgac agctacaaca    240
cgcgagagaa gaactgcctg gcatgaaac tgagtgaaga cggcacctac acgggtttca    300
tcaaagtgca tctgaaactc cggcggcctg tgacggtgcc tgctgggatc cggccccagt    360
ccatctatga tgccatcaag gaggtgaacc tggcggctac cacggacaag cggacatcct    420
tctacctgcc cctagatgcc atcaagcagc tgcacatcag cagcaccacc accgtcagtg    480
aggtcatcca ggggctgctc aagaagttca tggttgtgga caatcccag aagtttgcac    540 ttttttaagcg gatacacaag gacggacaag tgctcttcca gaaactctcc attgctgacc    600
gccccctcta cctgcgcctg cttgctgggc ctgacacgga ggtcctcaac tttgtgctaa    660
aggagaatga aactggagag gtagagtggg atgccttctc catccctgaa cttcagaact    720
tcctaacaat cctggaaaaa gaggagcagg acaaaatcca acaagtgcaa aagaagtatg    780
acaagtttag gcagaaactg gaggaggcct taagagaatc ccagggcaaa cctgggtaac    840
cggtcctgct cctctcctc ctggtgcatt cagatttatt tgtattatta attattattt    900
tgcaacagac acttttttctc aggacatctc tggcaggtgc atttgtgcct gcccagcagt    960
tccagctgtg gcaaaagtct cttccatgga caagtgtttg cacgggggtt cagctgtgcc   1020 cgccccagg ctgtgcccca ccacagattc tgccaaggat cagaactcat gtgaaacaaa   1080
cagctgacgt cctctctcga tctgcaagcc tttcaccaac caaatagttg cctctctcgt   1140
caccaaactg gaacctcaca ccagccggca aggaaggaa gaaaggtttt agagctgtgt    1200
gttctttctc tggctttgat tcttctttga gttctcttac ttgccacgta caggaccatt   1260
atttatgagt gaaagttgt agcacattcc ttttgcaggt ctgagctaag cccttgaaag   1320
cagggtaatg ctcataaaag gactgttccc gcggccccaa ggtgcctgtt gttcacactt   1380
```

-continued

```
aagggaagtt tataaagcta ctggccccag atgctcaggg taaggagcac caaagctgag      1440
gctggctcag agatctccag agaagctgca gcctgccctg gccctggctc tggccctggc      1500
ccacattgca catggaaacc caaaggcata tatctgcgta tgtgtggtac ttagtcacat      1560
ctttgtcaac aaactgttcg tttttaagtt acaaatttga atttaatgtt gtcatcatcg      1620
tcatgtgttt ccccaaaggg aagccagtca ttgaccattt aaaaagtctc ctgctaagta      1680
tggaaatcag acagtaagag aaagccaaaa agcaatgcag agaaaggtgt ccaagctgtc      1740
ttcagccttc cccagctaaa gagcagagga gggcctgggc tacttgggtt ccccatcggc      1800
ctccagcact gcctccctcc tcccactgcg actctgggat ctccaggtgc tgcccaagga      1860
gttgccttga ttacagagag gggagcctcc aattcggcca acttggagtc ctttctgttt      1920
tgaagcatgg gccagacccg gcactgcgct cggagagccg gtgggcctgg cctccccgtc      1980
gacctcagtg ccttttgtt ttcagagaga aataggagta gggcgagttt gcctgaagct      2040
ctgctgctgg cttctcctgc caggaagtga acaatggcgg cggtgtggga gacaaggcca      2100
ggagagcccg cgttcagtat gggttgaggg tcacagacct ccctcccatc tgggtgcctg      2160
agttttgact ccaatcagtg ataccagacc acattgacag ggaggatcaa attcctgact      2220
tacatttgca ctggcttctt gtttaggctg aatcctaaaa taaattagtc aaaaaattcc      2280
aacaagtagc caggactgca gagacactcc agtgcagagg gagaaggact tgtaattttc      2340
aaagcagggc tggttttcca acccagcctc tgagaaacca tttctttgct atcctctgcc      2400
ttcccaagtc cctcttgggt cggttcaagc ccaagcttgt tcgtgtagct tcagaagttc      2460
cctctccgac ccaggctgag tccatactgc ccctgatccc agaaggaatg ctgacccctc      2520
gtcgtatgaa ctgtgcatag tctccagagc ttcaaaggca acacaagctc gcaactctaa      2580 gatttttta aaccacaaaa accctggtta gccatctcat gctcagcctt atcacttccc      2640
tccctttaga aactctctcc ctgctgtata ttaaagggag caggtggaga gtcattttcc      2700
ttcgtcctgc atgtctctaa cattaataga aggcatggct cctgctgcaa ccgctgtgaa      2760
tgctgctgag aacctccctc tatggggatg ctatttat ttttgagaag gaaaaaaaaa      2820
gtcatgtata tatacacata aaggcatata gctatatata aagagataag ggtgtttatg      2880
aaatgagaaa attattggac aattcagact ttactaaagc acagttagac ccaaggccta      2940
tgctgaggtc taaacctctg aaaaaagtat agtatcgagt acccgttccc tcccagaggt      3000
gggagtaact gctggtagtg ccttctttgg ttgtgttgct cagtgtgtaa gtgtttgttt      3060
ccaggatatt ttcttttaa atgtctttct tatatgggtt ttaaaaaaaa gtaataaaag      3120
cctgttgcaa aaatgaaaaa aaaa                                            3144
```

<210> SEQ ID NO 3
<211> LENGTH: 236
<212> TYPE: DNA
<213> ORGANISM: Homo sapiens
<220> FEATURE:
<221> NAME/KEY: misc_feature
<223> OTHER INFORMATION: Incyte ID No: 2201728H1
<221> NAME/KEY: unsure
<222> LOCATION: 9, 64
<223> OTHER INFORMATION: a, t, c, g, or other

<400> SEQUENCE: 3

```
ccttgatgng ctggcggcct cggccgggaa ctccggggta gatgaccgtg gacagcagca        60
tgancagtgg gtactgcagc ctggacgagg aactggaaga ctgcttcttc actgctaaga       120 ctacctttt cagaaatgcg cagagcaaac atctttcaaa gaatgtctgt aaacctgtgg       180
```

```
aggagacaca gcgcccgccc acactgcagg agatcaagca gaagatcgac agctac        236
```

```
<210> SEQ ID NO 4
<211> LENGTH: 510
<212> TYPE: DNA
<213> ORGANISM: Homo sapiens
<220> FEATURE:
<221> NAME/KEY: misc_feature
<223> OTHER INFORMATION: Incyte ID No: 2726173F6
<221> NAME/KEY: unsure
<222> LOCATION: 338, 498, 502, 506
<223> OTHER INFORMATION: a, t, c, g, or other

<400> SEQUENCE: 4
gagaggtaga gtgggatgcc ttctccatcc ctgaacttca gaacttccta acaatcctgg        60
aaaaagagga gcaggacaaa atccaacaag tgcaaaagaa gtatgacaag tttaggcaga       120
aactggagga ggccttaaga gaatcccagg caaacctgg gtaaccggtc ctgcttcctc       180
tcctcctggt gcattcagat ttatttgtat tattaattat tattttgcaa cagacacttt      240
ttctcaggac atctctggca ggtgcatttg tgcctgccca gcagttccag ctgtggcaaa      300
agtctcttcc atggacaagt gtttgcacgg gggttcantg tgcccgcccc caggctgtgc      360
cccaccacag atctgccaag gatcagaact catgtgaaca acagctgac gtcctctctc      420 gatctgcaag cctttcaacc aaccaaatag ttggctctct cgtaaccaaa ctggaacctc      480
acacccaggc cggcaaanga anggangaaa                                      510
```

```
<210> SEQ ID NO 5
<211> LENGTH: 604
<212> TYPE: DNA
<213> ORGANISM: Homo sapiens
<220> FEATURE:
<221> NAME/KEY: misc_feature
<223> OTHER INFORMATION: Incyte ID No: 1683926F6
<221> NAME/KEY: unsure
<222> LOCATION: 234, 249, 306, 365, 383, 427, 439, 442, 479, 482, 504,
    509, 540, 542,
<223> OTHER INFORMATION: a, t, c, g, or other

<400> SEQUENCE: 5
tgcctgccca gcagttccag ctgtggcaaa agtctcttcc atggacaagt gtttgcacgg        60
gggttcagct gtgcccgccc ccaggctgtg ccccaccaca gattctgcca aggatcagaa      120
ctcatgtgaa acaaacagct gacgtcctct ctcgatctgc aagcctttca ccaaccaaat      180
agttgcctct ctcgtcacca aactggaacc tcacaccagc cggcaaagga aggnagaaag      240
gttttaganc tgtgtgttct ttctctggca ttgattcttc tttgagttct cttacttgcc      300
acgtanagga cccattattt atgagtgaaa agttgtagca cattccttt gcaggtctga      360 gtaanccctg aaaacagggt aangctcata aaggatgtt cccgcgggcc caaggggcct      420
gttgttnaca cttaagggna gnttttaaag ctaatggccc caaatgttca ggggaaggng      480
cnccaaagct gaggctgggt ccanagatnt ccaaaaaagt tgagcttgcc ctggcctggn      540
tntgggcctg gccanattg ccatgggaac cccaaggta natcngngga nntgtggatt      600 aanc                                                                  604
```

```
<210> SEQ ID NO 6
<211> LENGTH: 568
<212> TYPE: DNA
<213> ORGANISM: Homo sapiens
<220> FEATURE:
<221> NAME/KEY: misc_feature
```

<223> OTHER INFORMATION: Incyte ID No: 1624086F6
<221> NAME/KEY: unsure
<222> LOCATION: 490, 553
<223> OTHER INFORMATION: a, t, c, g, or other

<400> SEQUENCE: 6

```
gtggtactta gtcacatctt tgtcaacaaa ctgttcgttt ttaagttaca aatttgaatt    60
taatgttgtc atcatcgtca tgtgtttccc caaagggaag ccagtcattg accatttaaa   120
aagtctcctg ctaagtatgg aaatcagaca gtaagagaaa gccaaaaagc aatgcagaga   180
aaggtgtcca agctgtcttc agccttcccc agctaaagag cagaggaggg cctgggctac   240
ttgggttccc catcggcctc cagcactgcc tccctcctcc cactgcgact ctgggatctc   300
caggtgctgc ccaaggagtt gccttgatta cagagagggg agcctccaat tcggccaact   360
tggagtcctt tctgttttga agcatgggcc agacccggca tgcgctcgga gaccggtggg   420
cctggcctcc ccgtcgacct cagtgctttt tgtttcagag agaaatagga gtaggcgag    480 tttgctgaan ctctgtgctg gcttctcctg ccaagaagtg aacaatggcg ggcggtgtgg   540
gagacaaggc cangagagcc cgcgttca                                      568
```

<210> SEQ ID NO 7
<211> LENGTH: 757
<212> TYPE: DNA
<213> ORGANISM: Homo sapiens
<220> FEATURE:
<221> NAME/KEY: misc_feature
<223> OTHER INFORMATION: Incyte ID No: 157250R1
<221> NAME/KEY: unsure
<222> LOCATION: 237, 397, 459, 474, 482, 509, 516, 578, 583, 589, 592,
      604, 610, 618,
<223> OTHER INFORMATION: a, t, c, g, or other

<400> SEQUENCE: 7

```
accatttaaa agtctcctgc taagtatggg aaatcagaca gtaagagaaa gccaaaaagc    60
aatgcagagg aaaggtgtcc aagctgtctt cagccttccc cagctaaaga gcagaggagg   120
gcctgggcta cttgggttcc ccatcggcct ccagcactgc ctccctcctc ccactgcgac   180
tctgggatct ccaggtgctg cccaaggagt tgccttgatt acagagaggg gagcctncaa   240
ttcggccaac ttggagtcct ttctgttttg aagcatgggc cagacccggc actgcgctcg   300
gagagccggt gggcctgggc ttcccgtcga cctcagtgcc ttttttgtttt cagagagaaa   360 taggagtagg gcgagtttgc ctgaagctct gctgctngct tctcctgcca ggaagtgaac   420
aatggcggcg gtgttggaga caaggccagg agagcccgng ttcaatattg gttnagggtc   480
anaagacctt ccttccaatt tggtgcctna gttttnactt ccaattcaag tgaattacca   540
gaccacaatt tacaaggagg gtcaaaattc tgacttanat ttnaattgnt tnttgtttaa   600
ggtnaatccn aaataaanta ggnaaaaaat tccacaagta gccaggcttn aagggcaatt   660
cagtgcaaga gggagaaggc cttntaattt naaaggaggg ntggttttca acccagcctt   720
ttngaaccat tttttnnnat ccnnnccttc caaagcc                             757
```

<210> SEQ ID NO 8
<211> LENGTH: 787
<212> TYPE: DNA
<213> ORGANISM: Homo sapiens
<220> FEATURE:
<221> NAME/KEY: misc_feature
<223> OTHER INFORMATION: Incyte ID No: 157250F1
<221> NAME/KEY: unsure
<222> LOCATION: 2, 574, 631, 644, 653, 666, 668, 671, 699, 723, 729,
      747, 760, 784

-continued

<223> OTHER INFORMATION: a, t, c, g, or other

<400> SEQUENCE: 8

| cngttttttt ttcattttg caacaggctt ttattactttt tttttaaaac ccatataaga | 60 |
| aagacattta aaagaaaat atcctggaaa caaacactta cacactgagc aacacaacca | 120 |
| aagaaggcac taccagcagt tactcccacc tctgggaggg aacgggtact cgatactata | 180 |
| cttttttcag aggtttagac ctcagcatag gccttgggtc taactgtgct ttagtaaagt | 240 |
| ctgaattgtc caataatttt ctcatttcat aaacacccctt atctctttat atatagctat | 300 |
| atgcctttat gtgtatatat acatgacttt tttttccctt ctcaaaaata aaatagccat | 360 |
| ccccatagag ggaggttctc agcagcattc acagcggttg cagcaggagc catgccttct | 420 |
| attaatgtta gagacatgca ggacgaagga aaatgactct ccacctgctc cctttaatat | 480 |
| acagcaggga gagagtttct aaagggaggg aagtgataag gctgaggcat gaggatggct | 540 |
| aaccagggtt tttgtggttt aaaaaaatct tagngttgcg agcttgtgtt gcctttgaag | 600 |
| ctctggagac tatgcacagt tcatacgacg ngggtcagc attncttctg ggntcagggg | 660 |
| cagttngnct nagctgggtc gggaggggac tttgaagcnc acgacaagt ttggcttgac | 720 |
| cgnccagng ggcttgggag gcagggntgc aagaatggtn tagggctggg ttggaaacag | 780 |
| cctntttt | 787 |

<210> SEQ ID NO 9
<211> LENGTH: 489
<212> TYPE: DNA
<213> ORGANISM: Homo sapiens
<220> FEATURE:
<221> NAME/KEY: misc_feature
<223> OTHER INFORMATION: Incyte ID No: 1208878R1
<221> NAME/KEY: unsure
<222> LOCATION: 157
<223> OTHER INFORMATION: a, t, c, g, or other

<400> SEQUENCE: 9

| agaaactctc tccctgctgt atattaaagg gagcaggtgg agagtcattt tccttcgtcc | 60 |
| tgcatgtctc taacattaat agaaggcatg gctcctgctg caaccgctgt gaatgctgct | 120 |
| gagaacctcc ctctatgggg atggctattt tattttngag aaggaaaaaa aaagtcatgt | 180 |
| atatatacac ataaaggcat atagctatat ataagagat aagggtgttt atgaaatgag | 240 |
| aaaattattg gacaattcag actttactaa agcacagtta gacccaaggc ctatgctgag | 300 |
| gtctaaacct ctgaaaaaag tatagtatcg agtacccgtt ccctcccaga ggtgggagta | 360 |
| actgctggta gtgccttctt tggttgtgtt gctcagtgtg taagtgtttg tttccaggat | 420 |
| attttctttt taaatgtctt tcttatatgg gttttaaaaa aaagtaataa aagcctgttg | 480 |
| caaaaatga | 489 |

<210> SEQ ID NO 10
<211> LENGTH: 278
<212> TYPE: DNA
<213> ORGANISM: Rattus norvegicus
<220> FEATURE:
<221> NAME/KEY: misc_feature
<223> OTHER INFORMATION: Incyte ID No: 700541810H1

<400> SEQUENCE: 10

| gcaaaagcac catgagctag cgactctgag gctgtgcatg ccatagcccc tggctccctg | 60 |
| ccgcctcagg ctcagcctta cactcccctc ccttgagaag tccccttcct gctgtgtatt | 120 |

```
acagggacat acggaaactc attcccttca tcctgcatgt gtgtagcatt aggagaaggc      180
atggctcctg ctgcaaacac tgtgaatgct gctcagacct ccctccatgg atggctattt      240 tattttttgac aagaaaaaaa attcatgtat atataaaa                             278

<210> SEQ ID NO 11
<211> LENGTH: 220
<212> TYPE: DNA
<213> ORGANISM: Rattus norvegicus
<220> FEATURE:
<221> NAME/KEY: misc_feature
<223> OTHER INFORMATION: Incyte ID No: 700632515H1

<400> SEQUENCE: 11
aagctgtgca ggcgcttgaa accccaatga aggaagcacg gactgcctgc ctgagagcag       60
cctggtaacc cactagaacc cgcacctgag ccagaacccg aagcccctc gcgcacccct      120 gccccgcagc agtccgatga gctcagactc gggcggggcc caatgaccgt agacagcagc     180
atgagcagcg ggtactgcag cctggatgag gaactggaag                           220

<210> SEQ ID NO 12
<211> LENGTH: 214
<212> TYPE: DNA
<213> ORGANISM: Rattus norvegicus
<220> FEATURE:
<221> NAME/KEY: misc_feature
<223> OTHER INFORMATION: Incyte ID No: 700540004H1

<400> SEQUENCE: 12
aaaatgtata tacatatata tgtatataca catagaggca tatagctata tataaagaaa       60
aggtgtttat tcagaaaggg atgatcaact tcagacttta aagcacagtt agacccggga     120
cctctactga ggttgagccg ctggaaacgt ggagttcctt aagtctcaga ggggtctaac     180
tgctggtagt gccttctatg gttgtatggc tctg                                 214

<210> SEQ ID NO 13
<211> LENGTH: 413
<212> TYPE: PRT
<213> ORGANISM: Rattus norvegicus
<220> FEATURE:
<221> NAME/KEY: misc_feature
<223> OTHER INFORMATION: Incyte ID No: g2459833

<400> SEQUENCE: 13

Met Ala Ser Pro Ala Ile Gly Gln Arg Pro Tyr Pro Leu Leu Leu
  1               5                  10                  15

Asp Pro Glu Pro Pro Arg Tyr Leu Gln Ser Leu Gly Gly Thr Glu
                 20                  25                  30

Pro Pro Pro Pro Ala Arg Pro Arg Arg Cys Ile Pro Thr Ala Leu
                 35                  40                  45

Ile Ser Ala Ser Gly Ala Ser Glu Gly Arg Gly Ser Arg Arg Asn
                 50                  55                  60

Ala Arg Gly Asp Pro Glu Pro Thr Pro Arg Asp Cys Arg His Ala
                 65                  70                  75

Arg Pro Val Arg Pro Gly Leu Gln Gln Arg Leu Arg Arg Pro
                 80                  85                  90

Gly Ser His Arg Pro Arg Asp Val Arg Ser Ile Phe Glu Gln Pro
                 95                 100                 105

Gln Asp Pro Arg Val Leu Ala Glu Arg Gly Glu Gly His Arg Phe
                110                 115                 120
```

-continued

```
Ala Glu Leu Ala Leu Arg Gly Gly Pro Gly Trp Cys Asp Leu Cys
            125                 130                 135

Gly Arg Glu Val Leu Arg Gln Ala Leu Arg Cys Ala Asn Cys Lys
            140                 145                 150

Phe Thr Cys His Pro Glu Cys Arg Ser Leu Ile Gln Leu Asp Cys
            155                 160                 165

Arg Gln Lys Glu Gly Pro Ala Leu Asp Arg Gln Ser Pro Glu Ser
            170                 175                 180

Thr Leu Thr Pro Thr Phe Asn Lys Asn Val Cys Lys Ala Val Glu
            185                 190                 195

Glu Thr Gln His Pro Pro Thr Ile Gln Glu Ile Lys Gln Lys Ile
            200                 205                 210

Asp Ser Tyr Asn Ser Arg Glu Lys His Cys Leu Gly Met Lys Leu
            215                 220                 225

Ser Glu Asp Gly Thr Tyr Thr Gly Phe Ile Lys Val His Leu Lys
            230                 235                 240

Leu Arg Arg Pro Val Thr Val Pro Ala Gly Ile Arg Pro Gln Ser
            245                 250                 255

Ile Tyr Asp Ala Ile Lys Glu Val Asn Pro Ala Ala Thr Thr Asp
            260                 265                 270

Lys Arg Thr Ser Phe Tyr Leu Pro Leu Asp Ala Ile Lys Gln Leu
            275                 280                 285

His Ile Ser Ser Thr Thr Val Ser Glu Val Ile Gln Gly Leu
            290                 295                 300

Leu Lys Lys Phe Met Val Val Asp Asn Pro Gln Lys Phe Ala Leu
            305                 310                 315

Phe Lys Arg Ile His Lys Asp Gly Gln Val Leu Phe Gln Lys Leu
            320                 325                 330

Ser Ile Ala Asp Cys Pro Leu Tyr Leu Arg Leu Leu Ala Gly Pro
            335                 340                 345

Asp Thr Asp Val Leu Ser Phe Val Leu Lys Glu Asn Glu Thr Gly
            350                 355                 360

Asp Val Glu Trp Asp Ala Phe Ser Ile Pro Glu Leu Gln Asn Phe
            365                 370                 375

Leu Thr Ile Leu Glu Lys Glu Gln Asp Lys Ile His Gln Leu
            380                 385                 390

Gln Lys Lys Tyr Asn Lys Phe Arg Gln Lys Leu Glu Glu Ala Leu
            395                 400                 405

Arg Glu Ser Gln Gly Lys Pro Gly
            410
```

<210> SEQ ID NO 14
<211> LENGTH: 413
<212> TYPE: PRT
<213> ORGANISM: Mus musculus
<220> FEATURE:
<221> NAME/KEY: misc_feature
<223> OTHER INFORMATION: Incyte ID No: g2997698

<400> SEQUENCE: 14

```
Met Ala Ser Pro Ala Ile Gly Gln Arg Pro Tyr Pro Leu Leu Leu
 1               5                  10                  15

Asp Pro Glu Pro Pro Arg Tyr Leu Gln Ser Leu Gly Gly Thr Glu
                20                  25                  30

Pro Pro Pro Pro Ala Arg Pro Arg Arg Cys Ile Pro Thr Ala Leu
                35                  40                  45
```

-continued

```
Ile Pro Ala Ala Gly Ala Ser Glu Asp Arg Gly Gly Arg Arg Ser
             50                  55                  60
Gly Arg Arg Asp Pro Glu Pro Thr Pro Arg Asp Cys Arg His Ala
             65                  70                  75
Arg Pro Val Arg Pro Gly Leu Gln Pro Arg Leu Arg Leu Arg Pro
             80                  85                  90
Gly Ser His Arg Pro Arg Asp Val Arg Ser Ile Phe Glu Gln Pro
             95                 100                 105
Gln Asp Pro Arg Val Leu Ala Glu Arg Gly Glu Gly His Arg Phe
            110                 115                 120
Val Glu Leu Ala Leu Arg Gly Gly Pro Gly Trp Cys Asp Leu Cys
            125                 130                 135
Gly Arg Glu Val Leu Arg Gln Ala Leu Arg Cys Ala Asn Cys Lys
            140                 145                 150
Phe Thr Cys His Ser Glu Cys Arg Ser Leu Ile Gln Leu Asp Cys
            155                 160                 165
Arg Gln Lys Gly Gly Pro Ala Leu Asp Arg Arg Ser Pro Gly Ser
            170                 175                 180
Thr Leu Thr Pro Thr Leu Asn Gln Asn Val Cys Lys Ala Val Glu
            185                 190                 195
Glu Thr Gln His Pro Pro Thr Ile Gln Glu Ile Lys Gln Lys Ile
            200                 205                 210
Asp Ser Tyr Asn Ser Arg Glu Lys His Cys Leu Gly Met Lys Leu
            215                 220                 225
Ser Glu Asp Gly Thr Tyr Thr Gly Phe Ile Lys Val His Leu Lys
            230                 235                 240
Leu Arg Arg Pro Val Thr Val Pro Ala Gly Ser Gly Pro Ser Pro
            245                 250                 255
Ser Met Asp Ala Ile Lys Glu Val Asn Pro Ala Ala Thr Thr Asp
            260                 265                 270
Lys Arg Thr Ser Phe Tyr Leu Pro Leu Asp Ala Ile Lys Gln Leu
            275                 280                 285
His Ile Ser Ser Thr Thr Thr Val Ser Glu Val Ile Gln Gly Leu
            290                 295                 300
Leu Lys Lys Phe Met Val Val Asp Asn Pro Gln Lys Phe Ala Leu
            305                 310                 315
Phe Lys Arg Ile His Lys Asp Gly Gln Val Leu Phe Gln Lys Leu
            320                 325                 330
Ser Ile Ala Asp Tyr Pro Leu Tyr Leu Arg Leu Leu Ala Gly Pro
            335                 340                 345
Asp Thr Asp Val Leu Ser Phe Val Leu Lys Glu Asn Glu Thr Gly
            350                 355                 360
Glu Val Glu Trp Asp Ala Phe Ser Ile Pro Glu Leu Gln Asn Phe
            365                 370                 375
Leu Thr Ile Leu Glu Lys Glu Glu Gln Asp Lys Ile His Gln Leu
            380                 385                 390
Gln Lys Lys Tyr Asn Lys Phe Arg Gln Lys Leu Glu Glu Ala Leu
            395                 400                 405
Arg Glu Ser Gln Gly Lys Pro Gly
            410
```

RAS ASSOCIATION DOMAIN CONTAINING PROTEIN

This application is a continuation-in-part of U.S. Ser. No. 09/023,655 filed Feb. 9, 1998 and U.S. Ser. No. 09/195,292 filed Nov. 18, 1998 now abandoned.

FIELD OF THE INVENTION

This invention relates to a mammalian cDNA which encodes a mammalian Ras association domain containing protein and to the use of the cDNA and the encoded protein in the diagnosis and treatment of cell proliferative and inflammatory disorders.

BACKGROUND OF THE INVENTION

Phylogenetic relationships among organisms have been demonstrated many times, and studies from a diversity of prokaryotic and eukaryotic organisms suggest a more or less gradual evolution of molecules, biochemical and physiological mechanisms, and metabolic pathways. Despite different evolutionary pressures, the proteins of nematode, fly, rat, and man have common chemical and structural is features and generally perform the same cellular function. Comparisons of the nucleic acid and protein sequences from organisms where structure and/or function are known accelerate the investigation of human sequences and allow the development of model systems for testing diagnostic and therapeutic agents for human conditions, diseases, and disorders.

Signal transduction is the general process by which cells respond to extracellular signals. In typical signal transduction pathways, binding of a signaling molecule such as a hormone, neurotransmitter, or growth factor to a cell membrane receptor is coupled to the action of an intracellular second messenger. G protein-coupled receptors (GPCRs) control intracellular processes through the activation of guanine nucleotide-binding proteins (G proteins). G proteins are heterotrimeric and consist of $\alpha$, $\beta$, and $\gamma$ subunits. The $\alpha$ subunit contains a guanine nucleotide binding domain and has GTPase activity. When GTP binds to the $\alpha$ subunit, it dissociates from the $\beta$ and $\gamma$ subunits and interacts with cellular target molecules. Hydrolysis of GTP to GDP serves as a molecular switch controlling the interactions of the $\alpha$ subunit with other proteins. The GDP bound form of the $\alpha$ subunit dissociates from its cellular target and reassociates with the $\beta$ and $\gamma$ subunits. A number of accessory proteins modulate G protein function by controlling their nucleotide state or membrane association. These regulatory molecules include exchange factors (GEFs) which stimulate GDP-GTP exchange, GTPase activating proteins (GAPs) which promote GTP hydrolysis, and guanine nucleotide dissociation inhibitors (GDIs) which inhibit guanine nucleotide dissociation and stabilize the GDP-bound form. G proteins can be classified into at least five subfamilies: Ras, Rho, Ran, Rab, and ADP-ribosylation factor, and they regulate various cell functions including cell growth and differentiation, cytoskeletal organization, and intracellular vesicle transport and secretion.

The Ras subfamily transduces signals from tyrosine kinase receptors, non-tyrosine kinase receptors, and heterotrimeric GPCRs (Fantl et al. (1993) Annu Rev Biochem 62:453–481; Woodrow et al. (1993) J Immunol 150:3853–3861; and Van Corven et al. (1993) Proc Natl Acad Sci 90:1257–1261). Stimulation of cell surface receptors activates Ras which, in turn, activates cytoplasmic kinases that control cell growth and differentiation. The first Ras targets identified were the Raf kinases (Avruch et al. (1994) Trends Biochem Sci 19:279–283). Interaction of Ras and Raf leads to activation of the MAP kinase cascade of serine/threonine kinases, which activate key transcription factors that control gene expression and protein synthesis (Barbacid (1987) Ann Rev Biochem 56:779–827; Treisman (1994) Curr Opin Genet Dev 4:96–101). Mutant Ras proteins, which bind but do not hydrolyze GTP, are constitutively activated, and cause continuous cell proliferation and cancer (Bos (1989) Cancer Res 49:4682–4689; Grunicke and Maly (1993) 4:389–402).

Ras regulates other signaling pathways by direct interaction with different cellular targets (Katz and McCormick (1997) Curr Opin Genet Dev 7:75–79). One such target is Ral GDS, a guanine nucleotide dissociation stimulator for the Ras-like GTPase, Ral (Albright et al. (1993) EMBO J 12:339–347). Ral GDS couples the Ras and Ral signaling pathways. Epidermal growth factor (EGF) stimulates the association of Ral GDS with Ras in mammalian cells, which activates the GEF activity of Ral GDS (Kikuchi and Williams (1996) J Biol Chem 271:588–594; Urano et al. (1996) EMBO J 15:810–816). Ral activation by Ral GDS leads to activation of Src, a tyrosine kinase that phosphorylates other molecules including transcription factors and components of the actin cytoskeleton (Goi et al. (2000) EMBO J 19:623–630). Ral interacts with a number of signaling molecules including Ral-binding protein, a GAP for the Rho-like GTPases; Cdc42 and Rac, which regulate cytoskeletal rearrangement; and phospholipase D1, which is involved in vesicular trafficking (Feig et al. (1996) Trends Biochem Sci 21:438–441; Voss et al. (1999) J Biol Chem 274:34691–34698).

Nore1 was identified from a yeast two-hybrid screen as a protein that interacts with Ras and Ras-related protein, Rap1b (Vavvas et al. (1998) J Biol Chem 273:5439–5442). It is a highly basic protein (pI=9.4) of 413 amino acids that contains a cysteine-histidine-rich region predicted to be a diacylglycerol/phorbol ester binding site, a proline-rich region at its N-terminus that may be an SH3 binding domain, and a Ras/Rap binding domain located at its C-terminus. Nore1 binds Ras in vitro in a GTP dependent manner. Experiments in vivo show that the association of Nore1 with Ras is dependent on EGF and 12-O-tetradecanoylphorbol-13-acetate activation in COS-7 cells and on EGF in KB cells.

Ras and other G proteins play roles in regulating the immune inflammatory response. Granulocytes, which include basophils, eosinophils, and neutrophils, play critical roles in inflammation. Eosinophils release toxic granule proteins, which kill microorganisms, and secrete prostaglandins, leukotrienes and cytokines, which amplify the inflammatory response. They sustain inflammation in allergic reactions and their malfunction can cause asthma and other allergic diseases. Interleukin-5 is a cytokine that regulates the growth, activation, and survival of eosinophils. The signal transduction mechanism of IL-5 in eosinophils involves the Ras-MAP kinase and Jak-Stat pathways (Pazdrak et al. (1995) J Exp Med 181:1827–1834; Adachi and Alam (1998) Am J Physiol 275:C623–633). Raf-1 kinase activation by Ras is implicated in eosinophil degranulation.

Neutrophils migrate to inflammatory sites where they eliminate pathogens by phagocytosis and release toxic products from their granules that kill microorganisms. G proteins, including Ras, Ral, Rac 1 and Rap1 regulate neutrophil function (M'Rabet et al. (1999) J Biol Chem 274:21847–21852). Rac1 may be involved in the respiratory burst of neutrophils. Ras and Rap1 are activated in response to the chemotactic agent, formyl methionine leucine phenylalanine (fMLP); the lipid mediator, platelet activating factor (PAF); and the cytokine, granulocyte-macrophage colony-stimulating factor (GM-CSF). Both Ras and Rap1 appear to play roles in neutrophil activation. Ral is activated by fMLP and PAF but not by GM-CSF and may be involved in chemotaxis, phagocytosis, or degranulation. Impairment of neutrophil function is associated with various inflammatory and autoimmune diseases.

The discovery of a mammalian cDNA encoding a new Ras target or effector satisfies a need in the art by providing compositions which are useful in the diagnosis and treatment of cell proliferative and inflammatory disorders.

SUMMARY OF THE INVENTION

The invention is based on the discovery of a mammalian cDNA which encodes a Ras association domain containing protein (RADCP) which is useful in the diagnosis and treatment of cell proliferative and inflammatory disorders, particularly thymus hyperplasia, allergies, asthma, and hypereosoinophilia.

The invention provides an isolated mammalian cDNA or a fragment thereof encoding a mammalian protein or a portion thereof selected from the group consisting of an amino acid sequence of SEQ ID NO:1, a variant having 80% identity to the amino acid sequence of SEQ ID NO:1, an antigenic epitope of SEQ ID NO:1, an oligopeptide of SEQ ID NO:1, and a biologically active portion of SEQ ID NO:1. The invention also provides an isolated mammalian cDNA or the complement thereof selected from the group consisting of a nucleic acid sequence of SEQ ID NO:2, a variant having at least 87% identity to the nucleic acid sequence of SEQ ID NO:2, a fragment of SEQ ID NOs:3–9, an oligonucleotide of SEQ ID NO:2. The invention additionally provides a composition, a substrate, and a probe comprising the cDNA, or the complement of the cDNA, encoding RADCP. The invention further provides a vector containing the cDNA, a host cell containing the vector and a method for using the cDNA to make RADCP. The invention still further provides a transgenic cell line or organism comprising the vector containing the cDNA encoding RADCP. The invention additionally provides a mammalian fragment or the complement thereof selected from the group consisting of SEQ ID NOs:10–12. In one aspect, the invention provides a substrate containing at least one of these fragments. In a second aspect, the invention provides a probe comprising the fragment which can be used in methods of detection, screening, and purification. In a further aspect, the probe is a single stranded complementary RNA or DNA molecule.

The invention provides a method for using a cDNA to detect the differential expression of a nucleic acid in a sample comprising hybridizing a probe to the nucleic acids, thereby forming hybridization complexes and comparing hybridization complex formation with a standard, wherein the comparison indicates the differential expression of the cDNA in the sample. In one aspect, the method of detection further comprises amplifying the nucleic acids of the sample prior to hybridization. In another aspect, the method showing differential expression of the cDNA is used to diagnose cell proliferative and inflammatory disorders, particularly thymus hyperplasia, allergies, asthma, and hypereosinophilia. In another aspect, the cDNA or a fragment or a complement thereof may comprise an element on an array.

The invention additionally provides a method for using a cDNA or a fragment or a complement thereof to screen a library or plurality of molecules or compounds to identify at least one ligand which specifically binds the cDNA, the method comprising combining the cDNA with the molecules or compounds under conditions allowing specific binding, and detecting specific binding to the cDNA, thereby identifying a ligand which specifically binds the cDNA. In one aspect, the molecules or compounds are selected from aptamers, DNA molecules, RNA molecules, peptide nucleic acids, artificial chromosome constructions, peptides, transcription factors, enhancers, repressors, and regulatory molecules.

The invention provides a purified mammalian protein or a portion thereof selected from the group consisting of an amino acid sequence of SEQ ID NO:1, a variant having 80% identity to the amino acid sequence of SEQ ID NO:1, an antigenic epitope of SEQ ID NO:1, an oligopeptide of SEQ ID NO:1, and a biologically active portion of SEQ ID NO:1. The invention also provides a composition comprising the purified protein or a portion thereof in conjunction with a pharmaceutical carrier. The invention further provides a method of using the RADCP to treat a subject with a cell proliferative or inflammatory disorder comprising administering to a patient in need of such treatment the composition containing the purified protein. The invention still further provides a method for using a protein to screen a library or a plurality of molecules or compounds to identify at least one ligand , the method comprising combining the protein with the molecules or compounds under conditions to allow specific binding and detecting specific binding, thereby identifying a ligand which specifically binds the protein. In one aspect, the molecules or compounds are selected from DNA molecules, RNA molecules, peptide nucleic acids, peptides, proteins, mimetics, agonists, antagonists, antibodies, immunoglobulins, inhibitors, and drugs. In another aspect, the ligand is used to treat a subject with a cell proliferative or inflammatory disorder.

The invention provides a method of using a mammalian protein to screen a subject sample for antibodies which specifically bind the protein comprising isolating antibodies from the subject sample, contacting the isolated antibodies with the protein under conditions that allow specific binding, dissociating the antibody from the bound-protein, and comparing the quantity of antibody with known standards, wherein the presence or quantity of antibody is diagnostic of cell proliferative and inflammatory disorders, particularly thymus hyperplasia, allergies, asthma, and hypereosoinophilia.

The invention also provides a method of using a mammalian protein to prepare and purify antibodies comprising immunizing a animal with the protein under conditions to elicit an antibody response, isolating animal antibodies, attaching the protein to a substrate, contacting the substrate with isolated antibodies under conditions to allow specific binding to the protein, dissociating the antibodies from the protein, thereby obtaining purified antibodies.

The invention provides a purified antibody which bind specifically to a polypeptide comprising the amino acid sequence selected from SEQ ID NO:1 and fragments thereof. The invention also provides a method of using an antibody to diagnose cell proliferative and inflammatory disorders, particularly thymus hyperplasia, allergies, asthma, and hypereosoinophilia comprising combining the antibody comparing the quantity of bound antibody to known standards, thereby establishing the presence of cell proliferative and inflammatory disorders. The invention further provides a method of using an antibody to treat cell proliferative and inflammatory disorders comprising administering to a patient in need of such treatment a pharmaceutical composition comprising the purified antibody.

The invention provides a method for inserting a marker gene into the genomic DNA of a mammal to disrupt the expression of the endogenous polynucleotide. The invention also provides a method for using a cDNA to produce a mammalian model system, the method comprising constructing a vector containing the cDNA selected from SEQ ID NOs:2–12, transforming the vector into an embryonic stem cell, selecting a transformed embryonic stem, microinjecting the transformed embryonic stem cell into a mammalian blastocyst, thereby forming a chimeric blastocyst, transferring the chimeric blastocyst into a pseudopregnant dam, wherein the dam gives birth to a chimeric offspring containing the cDNA in its germ line, and breeding the chimeric mammal to produce a homozygous, mammalian model system.

BRIEF DESCRIPTION OF THE FIGURES AND TABLES

FIGS. 1A, 1B, 1C, 1D, 1E, 1F, 1G, and 1H show the mammalian RADCP (2726173; SEQ ID NO:1) encoded by the cDNA (SEQ ID NO:2). The translation was produced using MACDNASIS PRO software (Hitachi Software Engineering, South San Francisco Calif.).

Figure 2A:
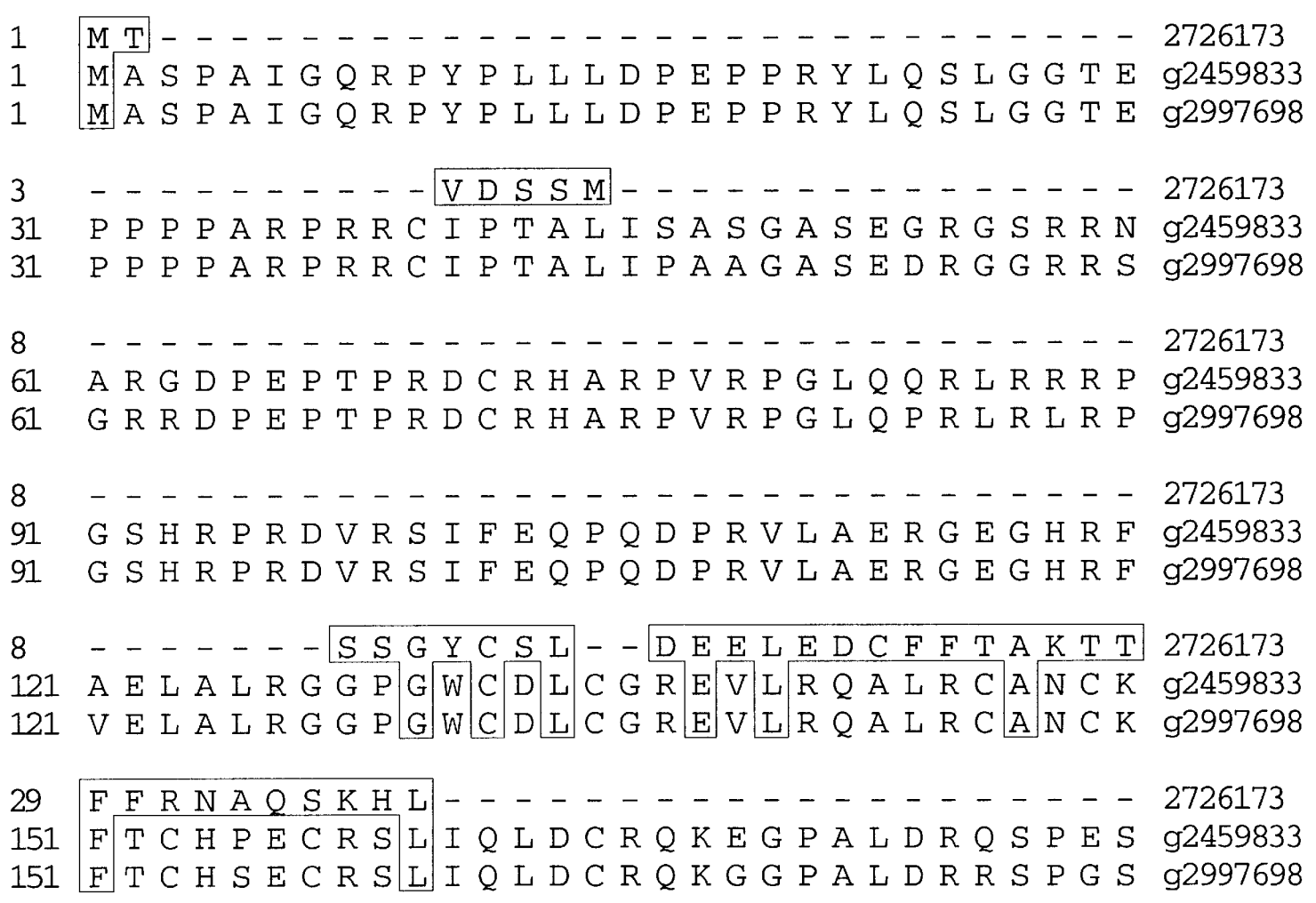

FIGS. 2A, 2B, and 2C show the amino acid sequence alignment between RADCP (2726173; SEQ ID NO:1), rat Maxp1 (g2459833; SEQ ID NO:13), and mouse Nore1 (g2997698; SEQ ID NO:14). The alignment was produced using the MEGALIGN program (DNASTAR, Madison Wis.).

Table 1 shows the expression analysis of RADCP. The northern analysis was produced using the LIFESEQ Gold database (Incyte Genomics, Palo Alto Calif.). Column 1 lists the tissue category to which the library is assigned; column 2, the total number of usable clones in the libraries (Clone count); column 3, the fraction of libraries in which the gene is found in the selected tissue category (Found in); column 4, the number of distinct clones of the gene expressed in the selected libraries (Abs Abund); column 5, the percentage abundance calculated from the number of clones of the gene from the selected libraries relative to the total number of clones from the selected libraries (Pct Abund); column 6, percentage specificity calculated from the number of clones of the gene expressed in the selected tissue category relative to the total number of clones of the gene in all tissue categories (Pct Spec).

Table 2 shows expression of RADCP in the hemic and immune system. Column 1 lists the library name (Library ID); column 2, the total number of usable clones in the library (Clone count); column 3, the library description; column 4, the number of distinct clones of the gene expressed in the selected libraries; column 5 (Abs Abund), the percentage abundance calculated from the number of clones of the gene isolated from the selected libraries relative to the total number of clones from the selected libraries (Pct Abund); column 6, percentage specificity calculated from the number of clones of the gene expressed in the selected tissue category relative to the total number of clones of the gene in all tissue categories (Pct Spec).

DESCRIPTION OF THE INVENTION

It is understood that this invention is not limited to the particular machines, materials and methods described. It is also to be understood that the terminology used herein is for the purpose of describing particular embodiments and is not intended to limit the scope of the present invention which will be limited only by the appended claims. As used herein, the singular forms "a", "an", and "the" include plural reference unless the context clearly dictates otherwise. For example, a reference to "a host cell" includes a plurality of such host cells known to those skilled in the art.

Unless defined otherwise, all technical and scientific terms used herein have the same meanings as commonly understood by one of ordinary skill in the art to which this invention belongs. All publications mentioned herein are cited for the purpose of describing and disclosing the cell lines, protocols, reagents and vectors which are reported in the publications and which might be used in connection with the invention. Nothing herein is to be construed as an admission that the invention is not entitled to antedate such disclosure by virtue of prior invention.

Definitions

"RADCP" refers to a substantially purified protein obtained from any mammalian species, including bovine, canine, murine, ovine, porcine, rodent, simian, and preferably the human species, and from any source, whether natural, synthetic, semi-synthetic, or recombinant.

"Array" refers to an ordered arrangement of at least two cDNAs on a substrate. At least one of the cDNAs represents a control or standard sequence, and the other, a cDNA of diagnostic interest. The arrangement of from about two to about 40,000 cDNAs on the substrate assures that the size and signal intensity of each labeled hybridization complex formed between a cDNA and a sample nucleic acid is individually distinguishable.

The "complement" of a cDNA of the Sequence Listing refers to a nucleic acid molecule which is completely complementary over its full length and which will hybridize to the cDNA or an mRNA under conditions of high stringency.

"cDNA" refers to an isolated polynucleotide, nucleic acid molecule, or any fragment or complement thereof. It may have originated recombinantly or synthetically, be double-stranded or single-stranded, represent coding and/or non-coding sequence, an exon with or without an intron from a genomic DNA molecule.

The phrase "cDNA encoding a protein" refers to a nucleic acid sequence that closely aligns with sequences which encode conserved regions, motifs or domains that were identified by employing analyses well known in the art. These analyses include BLAST (Basic Local Alignment Search Tool; Altschul (1993) J Mol Evol 36: 290–300; Altschul et al. (1990) J Mol Biol 215:403–410) which provdes identity within the conserved region.

"Derivative" refers to a cDNA or a protein that has been subjected to a chemical modification. Derivatization of a cDNA can involve substitution of a nontraditional base such as queosine or of an analog such as hypoxanthine. These substitutions are well known in the art. Derivatization of a protein involves the replacement of a hydrogen by an acetyl, acyl, alkyl, amino, formyl, or morpholino group. Derivative molecules retain the biological activities of the naturally occurring molecules but may confer advantages such as longer lifespan or enhanced activity.

"Differential expression" refers to an increased, upregulated or present, or decreased, downregulated or absent, gene expression as detected by the absence, presence, or at least two-fold changes in the amount of transcribed messenger RNA or translated protein in a sample.

"Disorder" refers to conditions, diseases or syndromes in which the cDNAs and RADCP are differentially expressed, particularly cell proliferative and inflammatory disorders such as thymus hyperplasia, allergies, asthma, and hypereosinophilia.

"Fragment" refers to a chain of consecutive nucleotides from about 200 to about 700 base pairs in length. Fragments may be used in PCR or hybridization technologies to identify related nucleic acid molecules and in binding assays to screen for a ligand. Nucleic acids and their ligands identified in this manner are useful as therapeutics to regulate replication, transcription or translation.

A "hybridization complex" is formed between a cDNA and a nucleic acid of a sample when the purines of one molecule hydrogen bond with the pyrimidines of the complementary molecule, e.g., 5'-A-G-T-C-3' base pairs with 3'-T-C-A-G-5'. The degree of complementarity and the use of nucleotide analogs affect the efficiency and stringency of hybridization reactions.

"Ligand" refers to any agent, molecule, or compound which will bind specifically to a complementary site on a cDNA molecule or polynucleotide, or to an epitope or a protein. Such ligands stabilize or modulate the activity of polynucleotides or proteins and may be composed of inorganic or organic substances including nucleic acids, proteins, carbohydrates, fats, and lipids.

"Oligonucleotide" refers a single stranded molecule from about 18 to about 60 nucleotides in length which may be used in hybridization or amplification technologies or in regulation of replication, transcription or translation. Substantially equivalent terms are amplimer, primer, and oligomer.

"Portion" refers to any part of a protein used for any purpose; but especially, to an epitope for the screening of ligands or for the production of antibodies.

"Post-translational modification" of a protein can involve lipidation, glycosylation, phosphorylation, acetylation, racemization, proteolytic cleavage, and the like. These processes may occur synthetically or biochemically. Biochemical modifications will vary by cellular location, cell type, pH, enzymatic milieu, and the like.

"Probe" refers to a cDNA that hybridizes to at least one nucleic acid in a sample. Where targets are single stranded, probes are complementary single strands. Probes can be labeled with reporter molecules for use in hybridization reactions including Southern, northern, in situ, dot blot, array, and like technologies or in screening assays.

"Protein" refers to a polypeptide or any portion thereof. A "portion" of a protein refers to that length of amino acid sequence which would retain at least one biological activity, a domain identified by PFAM or PRINTS analysis or an antigenic epitope of the protein identified using Kyte-Doolittle algorithms of the PROTEAN program (DNASTAR, Madison Wis.). An "oligopeptide" is an amino acid sequence from about five residues to about 15 residues that is used as part of a fusion protein to produce an antibody.

"Purified" refers to any molecule or compound that is separated from its natural environment and is from about 60% free to about 90% free from other components with which it is naturally associated.

"Sample" is used in its broadest sense as containing nucleic acids, proteins, antibodies, and the like. A sample may comprise a bodily fluid; the soluble fraction of a cell preparation, or an aliquot of media in which cells were grown; a chromosome, an organelle, or membrane isolated or extracted from a cell; genomic DNA, RNA, or cDNA in solution or bound to a substrate; a cell; a tissue; a tissue print; a fingerprint, buccal cells, skin, or hair; and the like.

"Specific binding" refers to a special and precise interaction between two molecules which is dependent upon their structure, particularly their molecular side groups. For example, the intercalation of a regulatory protein into the major groove of a DNA molecule, the hydrogen bonding along the backbone between two single stranded nucleic acids, or the binding between an epitope of a protein and an agonist, antagonist, or antibody.

"Similarity" as applied to sequences, refers to the quantification (usually percentage) of nucleotide or residue matches between at least two sequences aligned using a standardized algorithm such as Smith-Waterman alignment (Smith and Waterman (1981) J Mol Biol 147:195–197) or BLAST2 (Altschul et al. (1997) Nucleic Acids Res 25:3389–3402). BLAST2 may be used in a standardized and reproducible way to insert gaps in one of the sequences in order to optimize alignment and to achieve a more meaningful comparison between them.

"Substrate" refers to any rigid or semi-rigid support to which cDNAs or proteins are bound and includes membranes, filters, chips, slides, wafers, fibers, magnetic or nonmagnetic beads, gels, capillaries or other tubing, plates, polymers, and microparticles with a variety of surface forms including wells, trenches, pins, channels and pores.

"Variant" refers to molecules that are recognized variations of a cDNA or a protein encoded by the cDNA. Splice variants may be determined by BLAST score, wherein the score is at least 100, and most preferably, at least 400. Allelic variants have a high percent identity to the cDNAs and may differ by about three bases per hundred bases. "Single nucleotide polymorphism" (SNP) refers to a change in a single base as a result of a substitution, insertion or deletion. The change may be conservative (purine for purine) or non-conservative (purine to pyrimidine) and may or may not result in a change in an encoded amino acid.

THE INVENTION

The invention is based on the discovery of a cDNA which encodes RADCP and on the use of the cDNA, or fragments thereof, and protein, or portions thereof, as compositions in the characterization, diagnosis, and treatment of cell proliferative and inflammatory disorders, particularly thymus hyperplasia, allergies, asthma, and hypereosinophilia.

The present invention was discovered using a method for identifying gene sequences which coexpress with known genes associated with inflammation in a plurality of samples. The known inflammation genes include CD16, L-selectin, Src-like adapter protein (SLAP), IP-30, superoxidase homoenzyme subunits (p67phox, p47phox, and p40phox), alpha-1-antitrypsin (AAT), C1q-A, 5-lipoxygenase activating protein (FLAP), and SRC family tyrosine kinase (HCK). The literature associated with the selection of known genes and the statistical methods for determining the probability of coexpression (p-value) are described in U.S. Ser. No. 09/195,292 incorporated by reference herein. In the table below, column 1 lists the genes that coexpressed with RADCP and column 2 lists the negative log of the p-value (−log p) for the coexpression of RADCP.

| Genes expressed during inflammation | (-log p) for coexpression with RADCP |
|---|---|
| CD16 | 3 |
| L-selectin | 8 |
| SLAP | 5 |
| IP-30 | 4 |
| P67phox | 6 |
| P47phox | 7 |
| P40phox | 2 |
| AAT | 2 |
| CLq-A | 0 |
| FLAP | 3 |
| HCK | 5 |

The cDNA encoding RADCP of the present invention was first identified by BLAST homology between the translation of Incyte Clone 2726173 from the ovarian tumor cDNA library (OVARTUT05) and rat Maxp1 (g2459833; SEQ ID NO:13) and mouse Nore1 (g2997698; SEQ ID NO:14). The consensus sequence, SEQ ID NO:2 as shown in FIGS. 1A–1H, was derived from the following overlapping and/or extended nucleic acid sequences: Incyte Clones 2201728H1 (SPLNFET02), 2726173F6 (OVARTUT05), 1683926F6 (PROSNOT15), 1624086F6 (BRAITUT13), 157250R1 (THP1PLB02), 157250F1 (THPIPLB02), and 1208878R1 (BRSTNOT02) which are SEQ ID NOs:3–9, respectively. Useful fragments of the cDNA that encodes RADCP include the oligonucleotide from nucleotide 1 to nucleotide 50 of SEQ ID NO:1 or the complement thereof.

Tables 1 and 2 show the highly differential expression of the transcript encoding RADCP in the hemic and immune system, particularly in the spleen, eosinophils and other granulocytes, and macrophages. Overexpression of RADCP in eosinophil libraries (EOSINOT01, EOSINOT02, EOSINOT03) is associated with inflammatory disorders, particularly asthma and hypereosinophilia. RADCP shows increased expression in eosinophils and other granulocytes in response to factors known to stimulate the immune inflammatory response. RADCP shows increased expression in eosinophils in response to treatment with IL-5, a cytokine that promotes eosinophil production and activation, and in granulocytes treated with the cytokine, GM-CSF; the mitogen, lipopolysaccharide (LPS); and the chemotactic agent, fMLP. In addition, RADCP shows overexpression in a cDNA library from hyperplastic thymus (THYMDIT01).

Mammalian variants of the cDNA encoding RADCP were identified using BLAST2 with default parameters and the LIFESEQ or ZOOSEQ databases (Incyte Genomics). The mammalian variants of RADCP, SEQ ID NOs:10–12, are listed in the table below. Column 1 lists the SEQ ID NO; columm 2, the Incyte clone number; column 3, the library designation; column 4, the nucleotide overlap compared to SEQ ID NO:2; and column 5, the nucleotide identity compared to SEQ ID NO:2. These cDNAs are particularly useful for producing transgenic cell lines or organisms which model human disorders and upon which potential therapeutic treatments for such disorders may be tested.

| SEQ ID NO | Incyte Clone Number | Library Name | Homology Region | Nucleotide Identity |
|---|---|---|---|---|
| 10 | 700541810H1 | RACONOT01 | 2699–2834 | 87% |
| 11 | 700632515H1 | RATHNOT02 | 42–99 | 94% |

-continued

| SEQ ID NO | Incyte Clone Number | Library Name | Homology Region | Nucleotide Identity |
|---|---|---|---|---|
| 12 | 700540004H1 | RACONOT01 | 2829–2864 | 97% |
| | | | 3006–3034 | 96% |
| | | | 2915–2932 | 100% |

RADCP comprising the amino acid sequence of SEQ ID NO:1 is 265 amino acids in length. Pfam analysis indicates that the region of RADCP from A 119 to T211 is similar to a Ral GDS/AF-6 Ras association domain. This domain is found in RasGTP effectors. As shown in FIG. 2, RADCP has chemical and structural similarity with rat Maxp1 (g2459833; SEQ ID NO:13) and mouse Nore1 (g2997698; SEQ ID NO:14). In particular, RADCP and rat Maxp1 share 93% amino acid identity. RADCP and mouse Nore1 share 91% amino acid identity. The Ral GDS/AF-6 Ras association domain from residue A119 to T211 in RADCP is also found in rat Maxp1 and mouse Nore1. Exemplary portions of SEQ ID NO:1 are an antigenic epitope, residue F30 to residue M75 of SEQ ID NO:1 ( identified using the PROTEAN program (DNASTAR); and a biologically active portion, the conserved Ras association domain, residue A119 to residue T211 of SEQ ID NO:1.

The cDNA and fragments thereof (SEQ ID NOs:2–12) may be used in hybridization, amplification, and screening technologies to identify and distinguish among SEQ ID NO:2 and related molecules in a sample. The mammalian cDNAs may be used to produce transgenic cell lines or organisms which are model systems for human cell proliferative and inflammatory disorders, particularly thymus hyperplasia, allergies, asthma, and hypereosinophilia and upon which the toxicity and efficacy of potential therapeutic treatments may be tested. Toxicology studies, clinical trials, and subject/patient treatment profiles may be performed and monitored using the cDNAs, proteins, antibodies and molecules and compounds identified using the cDNAs and proteins of the present invention.

Characterization and Use of the Invention cDNA Libraries

In a particular embodiment disclosed herein, mRNA was isolated from mammalian cells and tissues using methods which are well known to those skilled in the art and used to prepare the cDNA libraries. The Incyte clones listed above were isolated from mammalian cDNA libraries. Three library preparations representative of the invention are described in the EXAMPLES below. The consensus sequences were chemically and/or electronically assembled from fragments including Incyte clones and extension and/or shotgun sequences using computer programs such as PHRAP (Green, University of Washington, Seattle Wash.), and AUTOASSEMBLER application (PE Biosystems, Foster City Calif.). Clones, extension and/or shotgun sequences are electronically assembled into clusters and/or master clusters.

Sequencing

Methods for sequencing nucleic acids are well known in the art and may be used to practice any of the embodiments of the invention. These methods employ enzymes such as the Klenow fragment of DNA polymerase I, SEQUENASE, Taq DNA polymerase and thermostable T7 DNA polymerase (Amersham Pharmacia Biotech (APB), Piscataway N.J.), or combinations of polymerases and proofreading exonucleases such as those found in the ELONGASE amplification system (Life Technologies, Gaithersburg Md.). Preferably, sequence preparation is automated with machines such MICROLAB 2200 system (Hamilton, Reno Nev.) and the DNA ENGINE thermal cycler (MJ Research, Watertown Mass.). Machines commonly used for sequencing include the ABI PRISM 3700, 377 or 373 DNA sequencing systems (PE Biosystems), the MEGABACE 1000 DNA sequencing system (APB), and the like. The sequences may be analyzed using a variety of algorithms well known in the art and described in Ausubel et al. (1997; *Short Protocols in Molecular Biology*, John Wiley & Sons, New York N.Y., unit 7.7) and in Meyers (1995; *Molecular Biology and Biotechnology*, Wiley VCH, New York N.Y., pp.856–853).

Shotgun sequencing may also be used to complete the sequence of a particular cloned insert of interest. Shotgun strategy involves randomly breaking the original insert into segments of various sizes and cloning these fragments into vectors. The fragments are sequenced and reassembled using overlapping ends until the entire sequence of the original insert is known. Shotgun sequencing methods are well known in the art and use thermostable DNA polymerases, heat-labile DNA polymerases, and primers chosen from representative regions flanking the cDNAs of interest. Incomplete assembled sequences are inspected for identity using various algorithms or programs such as CONSED (Gordon (1998) Genome Res 8:195–202) which are well known in the art. Contaminating sequences including vector or chimeric sequences or deleted sequences can be removed or restored, respectively, organizing the incomplete assembled sequences into finished sequences.

Extension of a Nucleic Acid Sequence

The sequences of the invention may be extended using various PCR-based methods known in the art. For example, the XL-PCR kit (PE Biosystems), nested primers, and commercially available cDNA or genomic DNA libraries may be used to extend the nucleic acid sequence. For all PCR-based methods, primers may be designed using commercially available software, such as OLIGO 4.06 primer analysis software (National Biosciences, Plymouth Minn.) to be about 22 to 30 nucleotides in length, to have a GC content of about 50% or more, and to anneal to a target molecule at temperatures from about 55 C. to about 68 C. When extending a sequence to recover regulatory elements, it is preferable to use genomic, rather than cDNA libraries.

Hybridization

The cDNA and fragments thereof can be used in hybridization technologies for various purposes. A probe may be designed or derived from unique regions such as the 5' regulatory region or from a nonconserved region (i.e., 5' or 3' of the nucleotides encoding the conserved catalytic domain of the protein) and used in protocols to identify naturally occurring molecules encoding the RADCP, allelic variants, or related molecules. The probe may be DNA or RNA, may be single stranded and should have at least 50% sequence identity to any of the nucleic acid sequences, SEQ ID NOs:2–12. Hybridization probes may be produced using oligolabeling, nick translation, end-labeling, or PCR amplification in the presence of a reporter molecule. A vector containing the cDNA or a fragment thereof may be used to produce an mRNA probe in vitro by addition of an RNA polymerase and labeled nucleotides. These procedures may be conducted using commercially available kits such as those provided by APB.

The stringency of hybridization is determined by G+C content of the probe, salt concentration, and temperature. In particular, stringency can be increased by reducing the concentration of salt or raising the hybridization temperature. In solutions used for some membrane based hybridizations, addition of an organic solvent such as formamide allows the reaction to occur at a lower temperature. Hybridization can be performed at low stringency with buffers, such as 5×SSC with 1% sodium dodecyl sulfate (SDS) at 60 C., which permits the formation of a hybridization complex between nucleic acid sequences that contain some mismatches. Subsequent washes are performed at higher stringency with buffers such as 0.2×SSC with 0.1% SDS at either 45 C. (medium stringency) or 68 C. (high stringency). At high stringency, hybridization complexes will remain stable only where the nucleic acids are completely complementary. In some membrane-based hybridizations, preferably 35% or most preferably 50%, formamide can be added to the hybridization solution to reduce the temperature at which hybridization is performed, and background signals can be reduced by the use of other detergents such as Sarkosyl or TRITON X-100 (Sigma-Aldrich St. Louis Mo.) and a blocking agent such as denatured salmon sperm DNA. Selection of components and conditions for hybridization are well known to those skilled in the art and are reviewed in Ausubel (supra) and Sambrook et al. (1989) *Molecular Cloning, A Laboratory Manual*, Cold Spring Harbor Press, Plainview N.Y.

Arrays may be prepared and analyzed using methods known in the art. Oligonucleotides may be used as either probes or targets in an array. The array can be used to monitor the expression level of large numbers of genes simultaneously and to identify genetic variants, mutations, and single nucleotide polymorphisms. Such information may be used to determine gene function; to understand the genetic basis of a condition, disease, or disorder; to diagnose a condition, disease, or disorder; and to develop and monitor the activities of therapeutic agents. (See, e.g., Brennan et al. (1995) U.S. Pat. No. 5,474,796; Schena et al. (1996) Proc Natl Acad Sci 93:10614–10619; Baldeschweiler et al. (1995) PCT application WO95/251116; Shalon et al. (1995) PCT application WO95/35505; Heller et al. (1997) Proc Natl Acad Sci 94:2150–2155; and Heller et al. (1997) U.S. Pat. No. 5,605,662.)

Hybridization probes are also useful in mapping the naturally occurring genomic sequence. The probes may be hybridized to: 1) a particular chromosome, 2) a specific region of a chromosome, or 3) artificial chromosome construction such as human artificial chromosome (HAC), yeast artificial chromosome (YAC), bacterial artificial chromosome (BAC), bacterial P1 construction, or single chromosome cDNA libraries.

Expression

Any one of a multitude of cDNAs encoding RADCP may be cloned into a vector and used to express the protein, or portions thereof, in host cells. The nucleic acid sequence can be engineered by such methods as DNA shuffling (U.S. Pat. No. 5,830,721) and site-directed mutagenesis to create new restriction sites, alter glycosylation patterns, change codon preference to increase expression in a particular host, produce splice variants, extend half-life, and the like. The expression vector may contain transcriptional and translational control elements (promoters, enhancers, specific initiation signals, and polyadenylated 3' sequence) from various sources which have been selected for their efficiency in a particular host. The vector, cDNA, and regulatory elements are combined using in vitro recombinant DNA techniques, synthetic techniques, and/or in vivo genetic recombination techniques well known in the art and described in Sambrook (supra, ch. 4, 8, 16 and 17).

A variety of host systems may be transformed with an expression vector. These include, but are not limited to, bacteria transformed with recombinant bacteriophage, plasmid, or cosmid DNA expression vectors; yeast transformed with yeast expression vectors; insect cell systems transformed with baculovirus expression vectors; plant cell systems transformed with expression vectors containing viral and/or bacterial elements, or animal cell systems (Ausubel supra, unit 16). For example, an adenovirus transcription/translation complex may be utilized in mammalian cells. After sequences are ligated into the E1 or E3 region of the viral genome, the infective virus is used to transform and express the protein in host cells. The Rous sarcoma virus enhancer or SV40 or EBV-based vectors may also be used for high-level protein expression.

Routine cloning, subcloning, and propagation of nucleic acid sequences can be achieved using the multifunctional PBLUESCRIPT vector (Stratagene, La Jolla Calif.) or PSPORT1 plasmid (Life Technologies). Introduction of a nucleic acid sequence into the multiple cloning site of these vectors disrupts the lacZ gene and allows colorimetric screening for transformed bacteria. In addition, these vectors may be useful for in vitro transcription, dideoxy sequencing, single strand rescue with helper phage, and creation of nested deletions in the cloned sequence.

For long term production of recombinant proteins, the vector can be stably transformed into cell lines along with a selectable or visible marker gene on the same or on a separate vector. After transformation, cells are allowed to grow for about 1 to 2 days in enriched media and then are transferred to selective media. Selectable markers, antimetabolite, antibiotic, or herbicide resistance genes, confer resistance to the relevant selective agent and allow growth and recovery of cells which successfully express the introduced sequences. Resistant clones identified either by survival on selective media or by the expression of visible markers, such as anthocyanins, green fluorescent protein (GFP), β glucuronidase, luciferase and the like, may be propagated using culture techniques. Visible markers are also used to quantify the amount of protein expressed by the introduced genes. Verification that the host cell contains the desired mammalian cDNA is based on DNA-DNA or DNA-RNA hybridizations or PCR amplification techniques.

The host cell may be chosen for its ability to modify a recombinant protein in a desired fashion. Such modifications include acetylation, carboxylation, glycosylation, phosphorylation, lipidation, acylation and the like. Post-translational processing which cleaves a "prepro" form may also be used to specify protein targeting, folding, and/or activity. Different host cells available from the ATCC (Manassas Va.) which have specific cellular machinery and characteristic mechanisms for post-translational activities may be chosen to ensure the correct modification and processing of the recombinant protein.

Recovery of Proteins from Cell Culture

Heterologous moieties engineered into a vector for ease of purification include glutathione S-transferase (GST), 6×His, FLAG, MYC, and the like. GST and 6-His are purified using commercially available affinity matrices such as immobilized glutathione and metal-chelate resins, respectively. FLAG and MYC are purified using commercially available monoclonal and polyclonal antibodies. For ease of separation following purification, a sequence encoding a proteolytic cleavage site may be part of the vector located between the protein and the heterologous moiety. Methods for recombinant protein expression and purification are discussed in Ausubel (supra, unit 16) and are commercially available.

Chemical Synthesis of Peptides

Proteins or portions thereof may be produced not only by recombinant methods, but also by using chemical methods well known in the art. Solid phase peptide synthesis may be carried out in a batchwise or continuous flow process which sequentially adds α-amino- and side chain-protected amino acid residues to an insoluble polymeric support via a linker group. A linker group such as methylamine-derivatized polyethylene glycol is attached to poly(styrene-co-divinylbenzene) to form the support resin. The amino acid residues are N-α-protected by acid labile Boc (t-butyloxycarbonyl) or base-labile Fmoc (9-fluorenylmethoxycarbonyl). The carboxyl group of the protected amino acid is coupled to the amine of the linker group to anchor the residue to the solid phase support resin. Trifluoroacetic acid or piperidine are used to remove the protecting group in the case of Boc or Fmoc, respectively. Each additional amino acid is added to the anchored residue using a coupling agent or pre-activated amino acid derivative, and the resin is washed. The full length peptide is synthesized by sequential deprotection, coupling of derivitized amino acids, and washing with dichloromethane and/or N,N-dimethylformamide. The peptide is cleaved between the peptide carboxy terminus and the linker group to yield a peptide acid or amide. (Novabiochem 1997/98 Catalog and Peptide Synthesis Handbook, San Diego Calif. pp. S1-S20). Automated synthesis may also be carried out on machines such as the ABI 431A peptide synthesizer (PE Biosystems). A protein or portion thereof may be substantially purified by preparative high performance liquid chromatography and its composition confirmed by amino acid analysis or by sequencing (Creighton (1984) *Proteins, Structures and Molecular Properties*, W H Freeman, New York N.Y.).

Preparation and Screening of Antibodies

Various hosts including goats, rabbits, rats, mice, humans, and others may be immunized by injection with RADCP or any portion thereof. Adjuvants such as Freund's, mineral gels, and surface active substances such as lysolecithin, pluronic polyols, polyanions, peptides, oil emulsions, keyhole limpet hemacyanin (KLH), and dinitrophenol may be used to increase immunological response. The oligopeptide, peptide, or portion of protein used to induce antibodies should consist of at least about five amino acids, more preferably ten amino acids, which are identical to a portion of the natural protein. Oligopeptides may be fused with proteins such as KLH in order to produce antibodies to the chimeric molecule.

Monoclonal antibodies may be prepared using any technique which provides for the production of antibodies by continuous cell lines in culture. These include, but are not limited to, the hybridoma technique, the human B-cell hybridoma technique, and the EBV-hybridoma technique. (See, e.g., Kohler et al. (1975) Nature 256:495–497; Kozbor et al. (1985) J. Immunol Methods 81:31–42; Cote et al. (1983) Proc Natl Acad Sci 80:2026–2030; and Cole et al. (1984) Mol Cell Biol 62:109–120.)

Alternatively, techniques described for the production of single chain antibodies may be adapted, using methods known in the art, to produce epitope specific single chain antibodies. Antibody fragments which contain specific binding sites for epitopes of the protein may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse et al. (1989) Science 246:1275–1281.)

The RADCP or a portion thereof may be used in screening assays of phagemid or B-lymphocyte immunoglobulin libraries to identify antibodies having the desired specificity. Numerous protocols for competitive binding or immunoassays using either polyclonal or monoclonal antibodies with established specificities are well known in the art. Such immunoassays typically involve the measurement of complex formation between the protein and its specific antibody. A two-site, monoclonal-based immunoassay utilizing monoclonal antibodies reactive to two non-interfering epitopes is preferred, but a competitive binding assay may also be employed (Pound (1998) *Immunochemical Protocols*, Humana Press, Totowa N.J.).

Labeling of Molecules for Assay

A wide variety of reporter molecules and conjugation techniques are known by those skilled in the art and may be used in various nucleic acid, amino acid, and antibody assays. Synthesis of labeled molecules may be achieved using commercially available kits (Promega, Madison Wis.) for incorporation of a labeled nucleotide such as $^{32}$P-dCTP (APB), Cy3-dCTP or Cy5-dCTP (Operon Technologies, Alameda Calif.), or amino acid such as $^{35}$S-methionine (APB). Nucleotides and amino acids may be directly labeled with a variety of substances including fluorescent, chemiluminescent, or chromogenic agents, and the like, by chemical conjugation to amines, thiols and other groups present in the molecules using reagents such as BIODIPY or FTIC (Molecular Probes, Eugene Oreg.).

Diagnostics

The cDNAs, fragments, oligonucleotides, complementary RNA and DNA molecules, and PNAs and may be used to detect and quantify differential gene expression in cell proliferative and inflammatory disorders, particularly thymus hyperplasia, allergies, asthma, and hypereosinophilia or to monitor mRNA levels during therapeutic intervention. Similarly antibodies which specifically bind RADCP may be used to quantitate the protein and to diagnose cell proliferative and inflammatory disorders, particularly thymus hyperplasia, allergies, asthma, and hypereosinophilia. The diagnostic assay may use hybridization or amplification technology to compare gene expression in a biological sample from a patient to standard samples in order to detect differential gene expression. Qualitative or quantitative methods for this comparison are well known in the art.

For example, the cDNA or probe may be labeled by standard methods and added to a biological sample from a patient under conditions for the formation of hybridization complexes. After an incubation period, the sample is washed and the amount of label (or signal) associated with hybridization complexes, is quantified and compared with a standard value. If complex formation in the patient sample is significantly altered (higher or lower) in comparison to either a normal or disease standard, then differential expression indicates the presence of a disorder.

In order to provide standards for establishing differential expression, normal and disease expression profiles are established. This is accomplished by combining a sample taken from normal subjects, either animal or human, with a cDNA under conditions for hybridization to occur. Standard hybridization complexes may be quantified by comparing the values obtained using normal subjects with values from an experiment in which a known amount of a substantially purified sequence is used. Standard values obtained in this manner may be compared with values obtained from samples from patients who were diagnosed with a particular condition, disease, or disorder. Deviation from standard values toward those associated with a particular disorder is used to diagnose that disorder.

Such assays may also be used to evaluate the efficacy of a particular therapeutic treatment regimen in animal studies and in clinical trial or to monitor the treatment of an individual patient. Once the presence of a condition is established and a treatment protocol is initiated, diagnostic assays may be repeated on a regular basis to determine if the level of expression in the patient begins to approximate that which is observed in a normal subject. The results obtained from successive assays may be used to show the efficacy of treatment over a period ranging from several days to months.

Immunological Methods

Detection and quantification of a protein using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes is preferred, but a competitive binding assay may be employed. (See, e.g., Coligan et al. (1997) *Current Protocols in Immunology*, Wiley-Interscience, New York N.Y.; Pound, supra.)

Therapeutics

Chemical and structural similarity exists between regions of RADCP (SEQ ID NO:1), rat Maxp1 (g2459833; SEQ ID NO:13), and mouse Nore1 (g2997698; SEQ ID NO:14), which all have Ral GDS/AF-6 Ras association domains as shown in FIG. 2. RADCP appears to play a role in cell prolierative and inflammatory disorders, particularly thymus hyperplasia, allergies, asthma, and hypereosinophilia. In the treatment of disorders associated with increased expression of the protein such as thymus hyperplasia, asthma, and hypereosinophilia, it is desirable to decrease expression or protein activity. In one embodiment, an inhibitor, antagonist or antibody of the protein may be administered to a subject to treat the disorder. In another embodiment, a composition comprising an inhibitor, antagonist or antibody in conjunction with a pharmaceutical carrier may be administered to a subject to treat the disorder associated with the increased expression or activity of the endogenous protein. In an additional embodiment, a vector expressing the complement of the cDNA or fragments thereof may be administered to a subject to treat the disorder.

Any of the cDNAs, complementary molecules, or fragments thereof, proteins or portions thereof, vectors delivering these nucleic acid molecules or expressing the proteins, and their ligands may be administered in combination with other therapeutic agents. Selection of the agents for use in combination therapy may be made by one of ordinary skill in the art according to conventional pharmaceutical principles. A combination of therapeutic agents may act synergistically to affect treatment of a particular disorder at a lower dosage of each agent.

Modification of Gene Expression Using Nucleic Acids

Gene expression may be modified by designing complementary or antisense molecules (DNA, RNA, or PNA) to the control, 5',3', or other regulatory regions of the gene encoding RADCP. Oligonucleotides designed with reference to the transcription initiation site are preferred. Similarly, inhibition can be achieved using triple helix base-pairing which inhibits the binding of polymerases, transcription factors, or regulatory molecules (Gee et al. In: Huber and Carr (1994)

*Molecular and Immunologic Approaches*, Futura Publishing, Mt. Kisco N.Y., pp. 163–177). A complementary molecule may also be designed to block translation by preventing binding between ribosomes and mRNA. In one alternative, a library or plurality of cDNAs or fragments thereof may be screened to identify those which specifically bind a regulatory, nontranslated sequence .

Ribozymes, enzymatic RNA molecules, may also be used to catalyze the specific cleavage of RNA. The mechanism of ribozyme action involves sequence-specific hybridization of the ribozyme molecule to complementary target RNA followed by endonucleolytic cleavage at sites such as GUA, GUU, and GUC. Once such sites are identified, an oligonucleotide with the same sequence may be evaluated for secondary structural features which would render the oligonucleotide inoperable. The suitability of candidate targets may also be evaluated by testing their hybridization with complementary oligonucleotides using ribonuclease protection assays.

Complementary nucleic acids and ribozymes of the invention may be prepared via recombinant expression, in vitro or in vivo, or using solid phase phosphoramidite chemical synthesis. In addition, RNA molecules may be modified to increase intracellular stability and half-life by addition of flanking sequences at the 5' and/or 3' ends of the molecule or by the use of phosphorothioate or 2' O-methyl rather than phosphodiesterase linkages within the backbone of the molecule. Modification is inherent in the production of PNAs and can be extended to other nucleic acid molecules. Either the inclusion of nontraditional bases such as inosine, queosine, and wybutosine, and or the modification of adenine, cytidine, guanine, thymine, and uridine with acetyl-, methyl-, thio- groups renders the molecule less available to endogenous endonucleases.

Screening and Purification Assays

The cDNA encoding RADCP may be used to screen a library of molecules or compounds for specific binding affinity. The libraries may be aptamers, DNA molecules, RNA molecules, peptides, and proteins such as transcription factors, enhancers, repressors, and other ligands which regulate the activity, replication, transcription, or translation of the cDNA in the biological system. The assay involves combining the cDNA or a fragment thereof with the library of molecules under conditions allowing specific binding, and detecting specific binding to identify at least one molecule which specifically binds the single stranded or, if appropriate, double stranded molecule.

In one embodiment, the polynucleotide of the invention may be incubated with a library of isolated and purified molecules or compounds and binding activity determined by methods well known in the art, e.g., a gel-retardation assay (U.S. Pat. No. 6,010,849) or a reticulocyte lysate transcriptional assay. In another embodiment, the polynucleotide may be incubated with nuclear extracts from biopsied and/or cultured cells and tissues. Specific binding between the polynucleotide and a molecule or compound in the nuclear extract is initially determined by gel shift assay and may be later confirmed by raising antibodies against that molecule or compound. When these antibodies are added into the assay, they cause a supershift in the gel-retardation assay.

In another embodiment, the polynucleotide may be used to purify a molecule or compound using affinity chromatography methods well known in the art. In one embodiment, the polynucleotide is chemically reacted with cyanogen bromide groups on a polymeric resin or gel. Then a sample is passed over and reacts with or binds to the polynucleotide. The molecule or compound which is bound to the polynucleotide may be released from the polynucleotide by increasing the salt concentration of the flow-through medium and collected.

In a further embodiment, the protein or a portion thereof may be used to purify a ligand from a sample. A method for using a mammalian protein or a portion thereof to purify a ligand would involve combining the protein or a portion thereof with a sample under conditions to allow specific binding, detecting specific binding between the protein and ligand, recovering the bound protein, and using an appropriate chaotropic agent to separate the protein from the purified ligand.

In a preferred embodiment, RADCP or a portion thereof may be used to screen a plurality of molecules or compounds in any of a variety of screening assays. The portion of the protein employed in such screening may be free in solution, affixed to an abiotic or biotic substrate (e.g. borne on a cell surface), or located intracellularly. For example, in one method, viable or fixed prokaryotic host cells that are stably transformed with recombinant nucleic acids that have expressed and positioned a peptide on their cell surface can be used in screening assays. The cells are screened against a plurality of ligands and the specificity of binding or formation of complexes between the expressed protein and the ligand may be measured. Specific binding between the protein and molecule may be measured. Depending on the kind of library being screened, the assay may be used to identify DNA molecules, RNA molecules, peptide nucleic acids, peptides, proteins, mimetics, agonists, antagonists, antibodies, immunoglobulins, inhibitors, and drugs or any other ligand, which specifically binds the protein.

In one aspect, this invention contemplate a method for high throughput screening using very small assay volumes and very small amounts of test compound as described in U.S. Pat. No. 5,876,946, incorporated herein by reference. This method is used to screen large numbers of molecules and compounds via specific binding. In another aspect, this invention also contemplates the use of competitive drug screening assays in which neutralizing antibodies capable of binding the protein specifically compete with a test compound capable of binding to the protein or oligopeptide or portion thereof. Molecules or compounds identified by screening may be used in a mammalian model system to evaluate their toxicity, diagnostic, or therapeutic potential.

Pharmacology

Pharmaceutical compositions are those substances wherein the active ingredients are contained in an effective amount to achieve a desired and intended purpose. The determination of an effective dose is well within the capability of those skilled in the art. For any compound, the therapeutically effective dose may be estimated initially either in cell culture assays or in animal models. The animal model is also used to achieve a desirable concentration range and route of administration. Such information may then be used to determine useful doses and routes for administration in humans.

A therapeutically effective dose refers to that amount of protein or inhibitor which ameliorates the symptoms or condition. Therapeutic efficacy and toxicity of such agents may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it may be expressed as the ratio, $LD_{50}/ED_{50}$. Pharmaceutical compositions which exhibit large therapeutic indexes are preferred. The data obtained from cell culture assays and animal studies are used in formulating a range of dosage for human use.

Model Systems

Animal models may be used as bioassays where they exhibit a phenotypic response similar to that of humans and where exposure conditions are relevant to human exposures. Mammals are the most common models, and most infectious agent, cancer, drug, and toxicity studies are performed on rodents such as rats or mice because of low cost, availability, lifespan, reproductive potential, and abundant reference literature. Inbred and outbred rodent strains provide a convenient model for investigation of the physiological consequences of under- or over-expression of genes of interest and for the development of methods for diagnosis and treatment of diseases. A mammal inbred to over-express a particular gene (for example, secreted in milk) may also serve as a convenient source of the protein expressed by that gene.

Toxicology

Toxicology is the study of the effects of agents on living systems. The majority of toxicity studies are performed on rats or mice. Observation of qualitative and quantitative changes in physiology, behavior, homeostatic processes, and lethality in the rats or mice are used to generate a toxicity profile and to assess potential consequences on human health following exposure to the agent.

Genetic toxicology identifies and analyzes the effect of an agent on the rate of endogenous, spontaneous, and induced genetic mutations. Genotoxic agents usually have common chemical or physical properties that facilitate interaction with nucleic acids and are most harmful when chromosomal aberrations are transmitted to progeny. Toxicological studies may identify agents that increase the frequency of structural or functional abnormalities in the tissues of the progeny if administered to either parent before conception, to the mother during pregnancy, or to the developing organism. Mice and rats are most frequently used in these tests because their short reproductive cycle allows the production of the numbers of organisms needed to satisfy statistical requirements.

Acute toxicity tests are based on a single administration of an agent to the subject to determine the symptomology or lethality of the agent. Three experiments are conducted: 1) an initial dose-range-finding experiment, 2) an experiment to narrow the range of effective doses, and 3) a final experiment for establishing the dose-response curve.

Subchronic toxicity tests are based on the repeated administration of an agent. Rat and dog are commonly used in these studies to provide data from species in different families. With the exception of carcinogenesis, there is considerable evidence that daily administration of an agent at high-dose concentrations for periods of three to four months will reveal most forms of toxicity in adult animals.

Chronic toxicity tests, with a duration of a year or more, are used to demonstrate either the absence of toxicity or the carcinogenic potential of an agent. When studies are conducted on rats, a minimum of three test groups plus one control group are used, and animals are examined and monitored at the outset and at intervals throughout the experiment.

Transgenic Animal Models

Transgenic rodents that over-express or under-express a gene of interest may be inbred and used to model human diseases or to test therapeutic or toxic agents. (See, e.g., U.S. Pat. Nos. 5,175,383 and 5,767,337.) In some cases, the introduced gene may be activated at a specific time in a specific tissue type during fetal or postnatal development. Expression of the transgene is monitored by analysis of phenotype, of tissue-specific mRNA expression, or of serum and tissue protein levels in transgenic animals before, during, and after challenge with experimental drug therapies.

Embryonic Stem Cells

Embryonic (ES) stem cells isolated from rodent embryos retain the potential to form embryonic tissues. When ES cells are placed inside a carrier embryo, they resume normal development and contribute to tissues of the live-born animal. ES cells are the preferred cells used in the creation of experimental knockout and knockin rodent strains. Mouse ES cells, such as the mouse 129/SvJ cell line, are derived from the early mouse embryo and are grown under culture conditions well known in the art. Vectors used to produce a transgenic strain contain a disease gene candidate and a marker gen, the latter serves to identify the presence of the introduced disease gene. The vector is transformed into ES cells by methods well known in the art, and transformed ES cells are identified and microinjected into mouse cell blastocysts such as those from the C57BL/6 mouse strain. The blastocysts are surgically transferred to pseudopregnant dams, and the resulting chimeric progeny are genotyped and bred to produce heterozygous or homozygous strains.

ES cells derived from human blastocysts may be manipulated in vitro to differentiate into at least eight separate cell lineages. These lineages are used to study the differentiation of various cell types and tissues in vitro, and they include endoderm, mesoderm, and ectodermal cell types which differentiate into, for example, neural cells, hematopoietic lineages, and cardiomyocytes.

Knockout Analysis

In gene knockout analysis, a region of a mammalian gene is enzymatically modified to include a non-mammalian gene such as the neomycin phosphotransferase gene (neo; Capecchi (1989) Science 244:1288–1292). The modified gene is transformed into cultured ES cells and integrates into the endogenous genome by homologous recombination. The inserted sequence disrupts transcription and translation of the endogenous gene. Transformed cells are injected into rodent blastulae, and the blastulae are implanted into pseudopregnant dams. Transgenic progeny are crossbred to obtain homozygous inbred lines which lack a functional copy of the mammalian gene. In one example, the mammalian gene is a human gene.

Knockin Analysis

ES cells can be used to create knockin humanized animals (pigs) or transgenic animal models (mice or rats) of human diseases. With knockin technology, a region of a human gene is injected into animal ES cells, and the human sequence integrates into the animal cell genome. Transformed cells are injected into blastulae and the blastulae are implanted as described above. Transgenic progeny or inbred lines are studied and treated with potential pharmaceutical agents to obtain information on treatment of the analogous human condition. These methods have been used to model several human diseases.

Non-Human Primate Model

The field of animal testing deals with data and methodology from basic sciences such as physiology, genetics, chemistry, pharmacology and statistics. These data are paramount in evaluating the effects of therapeutic agents on non-human primates as they can be related to human health. Monkeys are used as human surrogates in vaccine and drug evaluations, and their responses are relevant to human exposures under similar conditions. Cynomolgus and Rhesus monkeys (*Macaca fascicularis* and *Macaca mulatta*, respectively) and Common Marmosets (*Callithrix jacchus*) are the most common non-human primates (NHPs) used in these investigations. Since great cost is associated with developing and maintaining a colony of NHPs, early research and toxicological studies are usually carried out in rodent models. In studies using behavioral measures such as drug addiction, NHPs are the first choice test animal. In addition, NHPs and individual humans exhibit differential sensitivities to many drugs and toxins and can be classified as a range of phenotypes from "extensive metabolizers" to "poor metabolizers" of these agents.

In additional embodiments, the cDNAs which encode the mammalian protein may be used in any molecular biology techniques that have yet to be developed, provided the new techniques rely on properties of cDNAs that are currently known, including, but not limited to, such properties as the triplet genetic code and specific base pair interactions.

EXAMPLES

The examples below are provided to illustrate the subject invention and are not included for the purpose of limiting the invention. For purposes of example, preparation of the human tumorous ovary tissue (OVARTUT05) library will be described.

I cDNA Library Construction

The tissue for the OVARTUT05 library was obtained from a 62 year-old Caucasian female (specimen #0598A). Pathology indicated a grade 4 endometnoid carcinoma with extensive squamous differentiation forming a solid mass in the right ovary. The frozen tissue was homogenized and lysed in TRIZOL reagent (1 g tissue/10 ml; Life Technologies) using a POLYTRON homogenizer (PT-3000; Brinkmann Instruments, Westbury N.Y.). After a brief incubation on ice, chloroform was added (1:5 v/v), and the lysates were centrifuged. The upper chloroform layer was removed to a fresh tube and the RNA extracted with isopropanol, resuspended in DEPC-treated water, and treated with DNase for 25 min at 37° C. The RNA was re-extracted twice with acid phenol-chloroform, pH 4.7, and precipitated using 0.3M sodium acetate and 2.5 volumes ethanol. The mRNA was isolated with the OLIGOTEX kit (Qiagen, Chatsworth Calif.) and used to construct the cDNA library.

The mRNA was handled according to the recommended protocols in the SUPERSCRIPT plasmid system for cDNA synthesis and plasmid cloning (Life Technologies). The cDNAs were fractionated on a SEPHAROSE CL4B column (APB), and those cDNAs exceeding 400 bp were ligated into pINCY plasmid (Incyte Genomics). The plasmid was subsequently transformed into DH5α competent cells (Life Technologies).

II Construction of pINCY Plasmid

The plasmid was constructed by digesting the PSPORT1 plasmid (Life Technologies) with EcoRI restriction enzyme (New England Biolabs, Beverly Mass.) and filling the overhanging ends using Klenow enzyme (New England Biolabs) and 2'-deoxynucleotide 5'-triphosphates (dNTPs). The plasmid was self-ligated and transformed into the bacterial host, *E. coli* strain JM109.

An intermediate plasmid produced by the bacteria (PSPORT 1-ΔRI) showed no digestion with EcoRI and was digested with Hind III (New England Biolabs) and the overhanging ends were again filled in with Klenow and dNTPs. A linker sequence was phosphorylated, ligated onto the 5' blunt end, digested with EcoRI, and self-ligated. Following transformation into JM109 host cells, plasmids were isolated and tested for preferential digestibility with EcoRI, but not with Hind III. A single colony that met this criteria was designated pINCY plasmid.

After testing the plasmid for its ability to incorporate cDNAs from a library prepared using NotI and EcoRI restriction enzymes, several clones were sequenced; and a single clone containing an insert of approximately 0.8 kb was selected from which to prepare a large quantity of the plasmid. After digestion with NotI and EcoRI, the plasmid was isolated on an agarose gel and purified using a QIAQUICK column (Qiagen) for use in library construction.

III Isolation and Sequencing of cDNA Clones

Plasmid DNA was released from the cells and purified using either the MINIPREP kit (Edge Biosystems, Gaithersburg Md.) or the REAL PREP 96 plasmid kit (Qiagen). This kit consists of a 96-well block with reagents for 960 purifications. The recommended protocol was employed except for the following changes: 1) the bacteria were cultured in 1 ml of sterile terrific broth (BD Biosciences, Sparks Md.) with carbenicillin at 25 mg/l and glycerol at 0.4%; 2) after inoculation, the cells were cultured for 19 hours and then lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4 C.

The cDNAs were prepared for sequencing using the MICROLAB 2200 system (Hamilton) in combination with the DNA ENGINE thermal cyclers (MJ Research). The cDNAs were sequenced by the method of Sanger and Coulson (1975; J Mol Biol 94:441–448) using an ABI PRISM 377 sequencing system (PE Biosystems) or the MEGABACE 1000 DNA sequencing system (APB). Most of the isolates were sequenced according to standard ABI protocols and kits (PE Biosystems) with solution volumes of 0.25×–1.0×concentrations. In the alternative, cDNAs were sequenced using solutions and dyes from APB.

IV Extension of cDNA Sequences

The cDNAs were extended using the cDNA clone and oligonucleotide primers. One primer was synthesized to initiate 5' extension of the known fragment, and the other, to initiate 3' extension of the known fragment. The initial primers were designed using OLIGO 4.06 software (National Biosciences), to be about 22 to 30 nucleotides in length, to have a GC content of about 50% or more, and to anneal to the target sequence at temperatures of about 68 C. to about 72 C. Any stretch of nucleotides that would result in hairpin structures and primer-primer dimerizations was avoided.

Selected cDNA libraries were used as templates to extend the sequence. If more than one extension was necessary, additional or nested sets of primers were designed. Preferred libraries have been size-selected to include larger cDNAs and random primed to contain more sequences with 5' or upstream regions of genes. Genomic libraries are used to obtain regulatory elements, especially extension into the 5' promoter binding region.

High fidelity amplification was obtained by PCR using methods such as that taught in U.S. Pat. No. 5,932,451. PCR was performed in 96-well plates using the DNA ENGINE thermal cycler (MJ Research). The reaction mix contained DNA template, 200 nmol of each primer, reaction buffer containing $Mg^{2+}$, $(NH_4)_2SO_4$, and β-mercaptoethanol, Taq DNA polymerase (APB), ELONGASE enzyme (Life Technologies), and Pfu DNA polymerase (Stratagene), with the following parameters for primer pair PCI A and PCI B (Incyte Genomics): Step 1: 94 C., three min; Step 2: 94 C., 15 sec; Step 3: 60 C., one min; Step 4: 68 C., two min; Step 5: Steps 2, 3, and 4 repeated 20 times; Step 6: 68 C., five min; Step 7: storage at 4 C. In the alternative, the parameters for primer pair T7 and SK+ (Stratagene) were as follows: Step 1: 94 C., three min; Step 2: 94 C., 15 sec; Step 3: 57 C., one min; Step 4: 68 C., two min; Step 5: Steps 2, 3, and 4 repeated 20 times; Step 6: 68 C., five min; Step 7: storage at 4 C.

The concentration of DNA in each well was determined by dispensing 100 μl PICOGREEN quantitation reagent (0.25% reagent in 1×TE, v/v; Molecular Probes) and 0.5 μl of undiluted PCR product into each well of an opaque fluorimeter plate (Corning, Acton Mass.) and allowing the DNA to bind to the reagent. The plate was scanned in a Fluoroskan II (Labsystems Oy) to measure the fluorescence of the sample and to quantify the concentration of DNA. A 5 μl to 10 μl aliquot of the reaction mixture was analyzed by electrophoresis on a 1% agarose mini-gel to determine which reactions were successful in extending the sequence.

The extended clones were desalted, concentrated, transferred to 384-well plates, digested with CviJI cholera virus endonuclease (Molecular Biology Research, Madison Wis.), and sonicated or sheared prior to religation into pUC18 vector (APB). For shotgun sequences, the digested nucleotide sequences were separated on low concentration (0.6 to 0.8%) agarose gels, fragments were excised, and the agar was digested with AGARACE enzyme (Promega). Extended clones were religated using T4 DNA ligase (New England Biolabs) into pUC18 vector (APB), treated with Pfu DNA polymerase (Stratagene) to fill-in restriction site overhangs, and transfected into E. coli competent cells. Transformed cells were selected on antibiotic-containing media, and individual colonies were picked and cultured overnight at 37 C. in 384-well plates in LB/2×carbenicillin liquid media.

The cells were lysed, and DNA was amplified using primers, Taq DNA polymerase (APB) and Pfu DNA polymerase (Stratagene) with the following parameters: Step 1: 94 C., three min; Step 2: 94 C., 15 sec; Step 3: 60 C., one min; Step 4: 72 C., two min; Step 5: steps 2, 3, and 4 repeated 29 times; Step 6: 72 C., five min; Step 7: storage at 4 C. DNA was quantified using PICOGREEN quantitative reagent (Molecular Probes) as described above. Samples with low DNA recoveries were reamplified using the conditions described above. Samples were diluted with 20% dimethylsulfoxide (DMSO; 1:2, v/v), and sequenced using DYENAMIC energy transfer sequencing primers and the DYENAMIC DIRECT cycle sequencing kit (APB) or the ABI PRISM BIGDYE terminator cycle sequencing kit (PE Biosystems).

V Homology Searching of cDNA Clones and Their Deduced Proteins

The cDNAs of the Sequence Listing or their deduced amino acid sequences were used to query databases such as GenBank, SwissProt, BLOCKS, and the like. These databases that contain previously identified and annotated sequences or domains were searched using BLAST or BLAST 2 (Altschul et al. supra; Altschul, supra) to produce alignments and to determine which sequences were exact matches or homologs. The alignments were to sequences of prokaryotic (bacterial) or eukaryotic (animal, fungal, or plant) origin. Alternatively, algorithms such as the one described in Smith and Smith (1992, Protein Engineering 5:35–51) could have been used to deal with primary sequence patterns and secondary structure gap penalties. All of the sequences disclosed in this application have lengths of at least 49 nucleotides, and no more than 12% uncalled bases (where N is recorded rather than A, C, G, or T).

As detailed in Karlin (supra), BLAST matches between a query sequence and a database sequence were evaluated statistically and only reported when they satisfied the threshold of $10^{-25}$ for nucleotides and $10^{-14}$ for peptides. Homology was also evaluated by product score calculated as follows: the % nucleotide or amino acid identity [between the query and reference sequences] in BLAST is multiplied by the % maximum possible BLAST score [based on the lengths of query and reference sequences] and then divided by 100. In comparison with hybridization procedures used in the laboratory, the electronic stringency for an exact match was set at 70, and the conservative lower limit for an exact match was set at approximately 40 (with 1–2% error due to uncalled bases).

The BLAST software suite, freely available sequence comparison algorithms (NCBI, Bethesda Md.; http://www.ncbi.nlm.nih.gov/gor/b12.html), includes various sequence analysis programs including "blastn" that is used to align nucleic acid molecules and BLAST 2 that is used for direct pairwise comparison of either nucleic or amino acid molecules. BLAST programs are commonly used with gap and other parameters set to default settings, e.g.: Matrix: BLOSUM62; Reward for match: 1; Penalty for mismatch: −2; Open Gap: 5 and Extension Gap: 2 penalties; Gap x drop-off: 50; Expect: 10; Word Size: 11; and Filter: on. Identity is measured over the entire length of a sequence or some smaller portion thereof. Brenner et al. (1998; Proc Natl Acad Sci 95:6073–6078, incorporated herein by reference) analyzed the BLAST for its ability to identify structural homologs by sequence identity and found 30% identity is a reliable threshold for sequence alignments of at least 150 residues and 40%, for alignments of at least 70 residues.

The mammalian cDNAs of this application were compared with assembled consensus sequences or templates found in the LIFESEQ GOLD database. Component sequences from cDNA, extension, full length, and shotgun sequencing projects were subjected to PHRED analysis and assigned a quality score. All sequences with an acceptable quality score were subjected to various pre-processing and editing pathways to remove low quality 3' ends, vector and linker sequences, polyA tails, Alu repeats, mitochondrial and ribosomal sequences, and bacterial contamination sequences. Edited sequences had to be at least 50 bp in length, and low-information sequences and repetitive elements such as dinucleotide repeats, Alu repeats, and the like, were replaced by "Ns" or masked.

Edited sequences were subjected to assembly procedures in which the sequences were assigned to gene bins. Each sequence could only belong to one bin, and sequences in each bin were assembled to produce a template. Newly sequenced components were added to existing bins using BLAST and CROSSMATCH. To be added to a bin, the component sequences had to have a BLAST quality score greater than or equal to 150 and an alignment of at least 82% local identity. The sequences in each bin were assembled using PHRAP. Bins with several overlapping component sequences were assembled using DEEP PHRAP. The orientation of each template was determined based on the number and orientation of its component sequences.

Bins were compared to one another and those having local similarity of at least 82% were combined and reassembled. Bins having templates with less than 95% local identity were split. Templates were subjected to analysis by STITCHER/ EXON MAPPER algorithms that analyze the probabilities of the presence of splice variants, alternatively spliced exons, splice junctions, differential expression of alternative spliced genes across tissue types or disease states, and the like. Assembly procedures were repeated periodically, and templates were annotated using BLAST against GenBank databases such as GBpri. An exact match was defined as having from 95% local identity over 200 base pairs through 100% local identity over 100 base pairs and a homolog match as having an E-value (or probability score) of $\leq 1 \times 10^{-8}$. The templates were also subjected to frameshift FASTx against GENPEPT, and homolog match was defined as having an E-value of $\leq 1 \times 10^{-8}$. Template analysis and assembly was described in U.S. Ser. No. 09/276,534, filed Mar. 25, 1999.

Following assembly, templates were subjected to BLAST, motif, and other functional analyses and categorized in protein hierarchies using methods described in U.S. Ser. No. 08/812,290 and U.S. Ser. No. 08/811,758, both filed Mar. 6, 1997; in U.S. Ser. No. 08/947,845, filed Oct. 9, 1997; and in U.S. Ser. No. 09/034,807, filed Mar. 4, 1998. Then templates were analyzed by translating each template in all three forward reading frames and searching each translation against the PFAM database of hidden Markov model-based protein families and domains using the HMMER software package (Washington University School of Medicine, St. Louis Mo.; http://pfam.wustl.edu/).

The cDNA was further analyzed using MACDNASIS PRO software (Hitachi Software Engineering), and LASER- GENE software (DNASTAR) and queried against public databases such as the GenBank rodent, mammalian, vertebrate, prokaryote, and eukaryote databases, SwissProt, BLOCKS, PRINTS, PFAM, and Prosite.

VI Chromosome Mapping

Radiation hybrid and genetic mapping data available from public resources such as the Stanford Human Genome Center (SHGC), Whitehead Institute for Genome Research (WIGR), and Généthon are used to determine if any of the cDNAs presented in the Sequence Listing have been mapped. Any of the fragments of the cDNA encoding RADCP that have been mapped result in the assignment of all related regulatory and coding sequences mapping to the same location. The genetic map locations are described as ranges, or intervals, of human chromosomes. The map position of an interval, in cM (which is roughly equivalent to 1 megabase of human DNA), is measured relative to the terminus of the chromosomal p-arm.

VII Hybridization Technologies and Analyses

Immobilization of cDNAs on a Substrate

The cDNAs are applied to a substrate by one of the following methods. A mixture of cDNAs is fractionated by gel electrophoresis and transferred to a nylon membrane by capillary transfer. Alternatively, the cDNAs are individually ligated to a vector and inserted into bacterial host cells to form a library. The cDNAs are then arranged on a substrate by one of the following methods. In the first method, bacterial cells containing individual clones are robotically picked and arranged on a nylon membrane. The membrane is placed on LB agar containing selective agent (carbenicillin, kanamycin, ampicillin, or chloramphenicol depending on the vector used) and incubated at 37 C. for 16 hr. The membrane is removed from the agar and consecutively placed colony side up in 10% SDS, denaturing solution (1.5 M NaCl, 0.5 M NaOH ), neutralizing solution (1.5 M NaCl, 1 M Tris, pH 8.0), and twice in 2×SSC for 10 min each. The membrane is then UV irradiated in a STRATALINKER UV-crosslinker (Stratagene).

In the second method, cDNAs are amplified from bacterial vectors by thirty cycles of PCR using primers complementary to vector sequences flanking the insert. PCR amplification increases a starting concentration of 1–2 ng nucleic acid to a final quantity greater than 5 µg. Amplified nucleic acids from about 400 bp to about 5000 bp in length are purified using SEPHACRYL-400 beads (APB). Purified nucleic acids are arranged on a nylon membrane manually or using a dot/slot blotting manifold and suction device and are immobilized by denaturation, neutralization, and UV irradiation as described above. Purified nucleic acids are robotically arranged and immobilized on polymer-coated glass slides using the procedure described in U.S. Pat. No. 5,807, 522. Polymer-coated slides are prepared by cleaning glass microscope slides (Corning, Acton Mass.) by ultrasound in 0. 1% SDS and acetone, etching in 4% hydrofluoric acid (VWR Scientific Products, West Chester Pa.), coating with 0.05% aminopropyl silane (Sigma Aldrich) in 95% ethanol, and curing in a 110 C. oven. The slides are washed extensively with distilled water between and after treatments. The nucleic acids are arranged on the slide and then immobilized by exposing the array to UV irradiation using a STRATALINKER UV-crosslinker (Stratagene). Arrays are then washed at room temperature in 0.2% SDS and rinsed three times in distilled water. Non-specific binding sites are blocked by incubation of arrays in 0.2% casein in phosphate buffered saline (PBS; Tropix, Bedford Mass.) for 30 min at 60 C.; then the arrays are washed in 0.2% SDS and rinsed in distilled water as before.

Probe Preparation for Membrane Hybridization

Hybridization probes derived from the cDNAs of the Sequence Listing are employed for screening cDNAs, mRNAs, or genomic DNA in membrane-based hybridizations. Probes are prepared by diluting the cDNAs to a concentration of 40–50 ng in 45 µl TE buffer, denaturing by heating to 100 C. for five min, and briefly centrifuging. The denatured cDNA is then added to a REDIPRIME tube (APB), gently mixed until blue color is evenly distributed, and briefly centrifuged. Five µl of [$^{32}$P]dCTP is added to the tube, and the contents are incubated at 37 C. for 10 min. The labeling reaction is stopped by adding 5 µl of 0.2M EDTA, and probe is purified from unincorporated nucleotides using a PROBEQUANT G-50 microcolumn (APB). The purified probe is heated to 100 C. for five min, snap cooled for two min on ice, and used in membrane-based hybridizations as described below.

Probe Preparation for Polymer Coated Slide Hybridization

Hybridization probes derived from mRNA isolated from samples are employed for screening cDNAs of the Sequence Listing in array-based hybridizations. Probe is prepared using the GEMbright kit (Incyte Genomics) by diluting mRNA to a concentration of 200 ng in 9 µl TE buffer and adding 5 µl 5×buffer, 1 µl 0.1 M DTT, 3 µl Cy3 or Cy5 labeling mix, 1 µl RNase inhibitor, 1 µl reverse transcriptase, and 5 µl 1×yeast control mRNAs. Yeast control mRNAs are synthesized by in vitro transcription from noncoding yeast genomic DNA (W. Lei, unpublished). As quantitative controls, one set of control mRNAs at 0.002 ng, 0.02 ng, 0.2 ng, and 2 ng are diluted into reverse transcription reaction mixture at ratios of 1:100,000, 1:10,000, 1:1000, and 1:100 (w/w) to sample mRNA respectively. To examine mRNA differential expression patterns, a second set of control mRNAs are diluted into reverse transcription reaction mixture at ratios of 1:3, 3:1, 1:10, 10:1, 1:25, and 25:1 (w/w). The reaction mixture is mixed and incubated at 37 C. for two hr. The reaction mixture is then incubated for 20 min at 85 C., and probes are purified using two successive CHROMA SPIN+TE 30 columns (Clontech, Palo Alto Calif.). Purified probe is ethanol precipitated by diluting probe to 90 µl in DEPC-treated water, adding 2 µl 1 mg/ml glycogen, 60 µl 5 M sodium acetate, and 300 µl 100% ethanol. The probe is centrifuged for 20 min at 20,800×g, and the pellet is resuspended in 12 µl resuspension buffer, heated to 65 C. for five min, and mixed thoroughly. The probe is heated and mixed as before and then stored on ice. Probe is used in high density array-based hybridizations as described below.

Membrane-based Hybridization

Membranes are pre-hybridized in hybridization solution containing 1% Sarkosyl and 1×high phosphate buffer (0.5 M NaCl, 0.1 M $Na_2HPO_4$, 5 mM EDTA, pH 7) at 55 C. for two hr. The probe, diluted in 15 ml fresh hybridization solution, is then added to the membrane. The membrane is hybridized with the probe at 55 C. for 16 hr. Following hybridization, the membrane is washed for 15 min at 25 C. in 1 mM Tris (pH 8.0), 1% Sarkosyl, and four times for 15 min each at 25 C. in 1 mM Tris (pH 8.0). To detect hybridization complexes, XOMAT-AR film (Eastman Kodak, Rochester N.Y.) is exposed to the membrane overnight at −70 C., developed, and examined visually.

Polymer Coated Slide-based Hybridization

Probe is heated to 65 C. for five min, centrifuged five min at 9400 rpm in a 5415 C. microcentrifuge (Eppendorf Scientific, Westbury N.Y.), and then 18 µl is aliquoted onto the array surface and covered with a coverslip. The arrays are transferred to a waterproof chamber having a cavity just slightly larger than a microscope slide. The chamber is kept at 100% humidity internally by the addition of 140 µl of 5×SSC in a corner of the chamber. The chamber containing the arrays is incubated for about 6.5 hr at 60 C. The arrays are washed for 10 min at 45 C. in 1×SSC, 0.1% SDS, and three times for 10 min each at 45 C. in 0.1×SSC, and dried.

Hybridization reactions are performed in absolute or differential hybridization formats. In the absolute hybridization format, probe from one sample is hybridized to array elements, and signals are detected after hybridization complexes form. Signal strength correlates with probe mRNA levels in the sample. In the differential hybridization format, differential expression of a set of genes in two biological samples is analyzed. Probes from the two samples are prepared and labeled with different labeling moieties. A mixture of the two labeled probes is hybridized to the array elements, and signals are examined under conditions in which the emissions from the two different labels are individually detectable. Elements on the array that are hybridized to substantially equal numbers of probes derived from both biological samples give a distinct combined fluorescence (Shalon WO95/35505).

Hybridization complexes are detected with a microscope equipped with an Innova 70 mixed gas 10 W laser (Coherent, Santa Clara Calif.) capable of generating spectral lines at 488 nm for excitation of Cy3 and at 632 nm for excitation of Cy5. The excitation laser light is focused on the array using a 20× microscope objective (Nikon, Melville N.Y.). The slide containing the array is placed on a computer-controlled X-Y stage on the microscope and raster-scanned past the objective with a resolution of 20 micrometers. In the differential hybridization format, the two fluorophores are sequentially excited by the laser. Emitted light is split, based on wavelength, into two photomultiplier tube detectors (PMT R1477, Hamamatsu Photonics Systems, Bridgewater N.J.) corresponding to the two fluorophores. Appropriate filters positioned between the array and the photomultiplier tubes are used to filter the signals. The emission maxima of the fluorophores used are 565 nm for Cy3 and 650 nm for Cy5. The sensitivity of the scans is calibrated using the signal intensity generated by the yeast control mRNAs added to the probe mix. A specific location on the array contains a complementary DNA sequence, allowing the intensity of the signal at that location to be correlated with a weight ratio of hybridizing species of 1:100,000.

The output of the photomultiplier tube is digitized using a 12-bit RTI-835H analog-to-digital (A/D) conversion board (Analog Devices, Norwood Mass.) installed in an IBM-compatible PC computer. The digitized data are displayed as an image where the signal intensity is mapped using a linear 20-color transformation to a pseudocolor scale ranging from blue (low signal) to red (high signal). The data is also analyzed quantitatively. Where two different fluorophores are excited and measured simultaneously, the data are first corrected for optical crosstalk (due to overlapping emission spectra) between the fluorophores using the emission spectrum for each fluorophore. A grid is superimposed over the fluorescence signal image such that the signal from each spot is centered in each element of the grid. The fluorescence signal within each element is then integrated to obtain a numerical value corresponding to the average intensity of the signal. The software used for signal analysis is the GEMTOOLS program (Incyte Genomics).

VIII Electronic Analysis

BLAST was used to search for identical or related molecules in the GenBank or LIFESEQ databases (Incyte Genomics). The product score for human and rat sequences was calculated as follows: the BLAST score is multiplied by the % nucleotide identity and the product is divided by (5 times the length of the shorter of the two sequences), such that a 100% alignment over the length of the shorter sequence gives a product score of 100. The product score takes into account both the degree of similarity between two sequences and the length of the sequence match. For example, with a product score of 40, the match will be exact within a 1% to 2% error, and with a product score of at least 70, the match will be exact. Similar or related molecules are usually identified by selecting those which show product scores between 8 and 40.

Electronic northern analysis performed at a product score of 70 is shown in Tables 1 and 2. All sequences and cDNA libraries in the LIFESEQ database were categorized by system, organ/tissue and cell type. The categories included cardiovascular system, connective tissue, digestive system, embryonic structures, endocrine system, exocrine glands, female and male reproductive tissues, germ cells, hemic/immune system, liver, musculoskeletal system, nervous system, pancreas, respiratory system, sense organs, skin, stomatognathic system, unclassified/mixed, and the urinary tract. For each category, the number of libraries in which the sequence was expressed were counted and shown over the total number of libraries in that category. In a non-normalized library, expression levels of two or more are significant.

IX Complementary Molecules

Molecules complementary to the cDNA, from about 5 (PNA) to about 5000 bp (complement of a cDNA insert), are used to detect or inhibit gene expression. These molecules are selected using OLIGO 4.06 software (National Biosciences). Detection is described in Example VII. To inhibit transcription by preventing promoter binding, the complementary molecule is designed to bind to the most unique 5' sequence and includes nucleotides of the 5' UTR upstream of the initiation codon of the open reading frame. Complementary molecules include genomic sequences (such as enhancers or introns) and are used in "triple helix" base pairing to compromise the ability of the double helix to open sufficiently for the binding of polymerases, transcription factors, or regulatory molecules. To inhibit translation, a complementary molecule is designed to prevent ribosomal binding to the mRNA encoding the mammalian protein.

Complementary molecules are placed in expression vectors and used to transform a cell line to test efficacy; into an organ, tumor, synovial cavity, or the vascular system for transient or short term therapy; or into a stem cell, zygote, or other reproducing lineage for long term or stable gene therapy. Transient expression lasts for a month or more with a non-replicating vector and for three months or more if appropriate elements for inducing vector replication are used in the transformation/expression system.

Stable transformation of appropriate dividing cells with a vector encoding the complementary molecule can produce a transgenic cell line, tissue, or organism (U.S. Pat. No. 4,736,866). Those cells that assimilate and replicate sufficient quantities of the vector to allow stable integration also produce enough complementary molecules to compromise or entirely eliminate activity of the cDNA encoding the mammalian protein.

X Expression of RADCP

Expression and purification of the mammalian protein are achieved using either a mammalian cell expression system or an insect cell expression system. The pUB6NV5-His vector system (Invitrogen, Carlsbad Calif.) is used to express RADCP in CHO cells. The vector contains the selectable bsd gene, multiple cloning sites, the promoter/enhancer sequence from the human ubiquitin C gene, a C-terminal V5 epitope for antibody detection with anti-V5 antibodies, and a C-terminal polyhistidine (6×His) sequence for rapid purification on PROBOND resin (Invitrogen). Transformed cells are selected on media containing blasticidin.

Spodoptera frugiperda (Sf9) insect cells are infected with recombinant Autographica californica nuclear polyhedrosis virus (baculovirus). The polyhedrin gene is replaced with the mammalian cDNA by homologous recombination and the polyhedrin promoter drives cDNA transcription. The protein is synthesized as a fusion protein with 6×his which enables purification as described above. Purified protein is used in the following activity and to make antibodies.

XI Production of Antibodies

RADCP is purified using polyacrylamide gel electrophoresis and used to immunize mice or rabbits. Antibodies are produced using the protocols below. Alternatively, the amino acid sequence of RADCP is analyzed using LASERGENE software (DNASTAR) to determine regions of high antigenicity, and an antigenic epitope is selected, synthesized, and used to raise antibodies. Oligopeptides are synthesized using an ABI 431A peptide synthesizer (PE Biosystems) using Fmoc-chemistry and coupled to KLH (Sigma-Aldrich) by reaction with N-maleimidobenzoyl-N-hydroxysuccinimide ester.

Rabbits are immunized with the epitope-KLH complex in complete Freund's adjuvant. Immunizations are repeated at intervals thereafter in incomplete Freund's adjuvant. After a minimum of seven weeks for mouse or twelve weeks for rabbit, antisera are drawn and tested for antipeptide activity. Testing involves binding the peptide to plastic, blocking with 1% bovine serum albumin, reacting with rabbit antisera, washing, and reacting with radio-iodinated goat anti-rabbit IgG. Methods well known in the art are used to determine antibody titer and to prepare disease and control standards based on the amount of complex formation.

XII Purification of Naturally Occurring Protein Using Specific Antibodies

Naturally occurring or recombinant protein is purified by immunoaffinity chromatography using antibodies which specifically bind the protein. An immunoaffinity column is constructed by covalently coupling the antibody to CNBr-activated SEPHAROSE resin (APB). Media containing the protein is passed over the immunoaffinity column, and the column is washed using high ionic strength buffers in the presence of detergent to allow preferential absorbance of the protein. After coupling, the protein is eluted from the column using a buffer of pH 2–3 or a high concentration of urea or thiocyanate ion to disrupt antibody/protein binding, and the protein is collected.

XIII Screening Molecules for Specific Binding with the cDNA or Protein

The cDNA, or fragments thereof, or the protein, or portions thereof, are labeled with $^{32}$P-dCTP, Cy3-dCTP, or Cy5-dCTP (APB), or with BIODIPY or FTIC (Molecular Probes, Eugene Oreg.), respectively. Libraries of candidate molecules or compounds previously arranged on a substrate are incubated in the presence of labeled cDNA or protein. After incubation under conditions for either a nucleic acid or amino acid sequence, the substrate is washed, and any position on the substrate retaining label, which indicates specific binding or complex formation, is assayed, and the ligand is identified. Data obtained using different concentrations of the nucleic acid or protein are used to calculate affinity between the labeled nucleic acid or protein and the bound molecule.

XIV Two-Hybrid Screen

A yeast two-hybrid system, MATCHMAKER LexA Two-Hybrid system (Clontech Laboratories, Palo Alto Calif.), is used to screen for peptides that bind the mammalian protein of the invention. A cDNA encoding the protein is inserted into the multiple cloning site of a pLexA vector, ligated, and transformed into E. coli. cDNA, prepared from mRNA, is inserted into the multiple cloning site of a pB42AD vector, ligated, and transformed into E. coli to construct a cDNA library. The pLexA plasmid and pB42AD-cDNA library constructs are isolated from E. coli and used in a 2:1 ratio to co-transform competent yeast EGY48[p8op-lacZ] cells using a polyethylene glycol/lithium acetate protocol. Transformed yeast cells are plated on synthetic dropout (SD) media lacking histidine (−His), tryptophan (−Trp), and uracil (−Ura), and incubated at 30 C. until the colonies have grown up and can be counted. The colonies are pooled in a minimal volume of 1×TE (pH 7.5), replated on SD/-His/-Leu/-Trp/-Ura media supplemented with 2% galactose (Gal), 1% raffinose (Raf), and 80 mg/ml 5-bromo-4-chloro-3-indolyl β-d-galactopyranoside (X-Gal), and subsequently examined for growth of blue colonies. Interaction between expressed protein and cDNA fusion proteins activates expression of a LEU2 reporter gene in EGY48 and produces colony growth on media lacking leucine (−Leu). Interaction also activates expression of β-galactosidase from the p8oplacZ reporter construct that produces blue color in colonies grown on X-Gal.

Positive interactions between expressed protein and cDNA fusion proteins are verified by isolating individual positive colonies and growing them in SD/−Trp/−Ura liquid medium for 1 to 2 days at 30 C. A sample of the culture is plated on SD/−Trp/−Ura media and incubated at 30 C. until colonies appear. The sample is replica-plated on SD/−Trp/−Ura and SD/−His/−Trp/−Ura plates. Colonies that grow on SD containing histidine but not on media lacking histidine have lost the pLexA plasmid. Histidine-requiring colonies are grown on SD/Gal/Raf/X-Gal/−Trp/−Ura, and white colonies are isolated and propagated. The pB42AD-cDNA plasmid, which contains a cDNA encoding a protein that physically interacts with the mammalian protein, can be isolated from the yeast cells and characterized.

XVI RADCP Assay

RADCP is assayed for Ras binding by the method of Vavvas et al. (sura). RADCP is expressed as a GST fusion protein and the GST-RADCP fusion is incubated with Ras in the presence of either GTPγS or GDPβS. Glutathione-SEPHAROSE beads (APB) are added to recover the GST-RADCP fusion and GST-RADCP-Ras complexes from solution. Proteins are eluted from the glutathione-SEPHAROSE beads with SDS sample buffer and separated by SDS-PAGE. Following electrophoresis, proteins are transferred to a PVDF membrane (APB) and probed for Ras with monoclonal anti-Ras antibodies.

All patents and publications mentioned in the specification are incorporated by reference herein. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the field of molecular biology or related fields are intended to be within the scope of the following claims.

What is claimed is:

1. An isolated cDNA encoding a protein selected from:
   a) a protein having an amino acid sequence of SEQ ID NO:1; and
   b) an antigenic epitope of a protein having an amino acid sequence of SEQ ID NO:1.

2. The composition comprising the cDNA or the complement of the cDNA of claim 1 and a reporter molecule.

3. A substrate comprising the cDNA or the complement of the cDNA of claim 1.

4. A probe comprising the cDNA or the complement of the cDNA of claim 1.

5. A method for using a cDNA to detect the differential expression of a nucleic acid in a sample comprising:
   a) hybridizing the probe of claim 4 to the nucleic acids, thereby forming hybridization complexes; and
   b) comparing hybridization complex formation with a standard, wherein the comparison indicates the differential expression of the cDNA in the sample.

6. The method of claim 5 further comprising amplifying the nucleic acids of the sample prior to hybridization.

7. The method of claim 5 wherein detection of differential expression of the cDNA is diagnostic of cell proliferative and inflammatory disorders, particularly thymus hyperplasia, allergies, asthma, and hypereosinophilia.

8. A vector comprising the cDNA of claim 1.

9. A host cell comprising the vector of claim 8.

10. A method for producing a protein, the method comprising:
    a) culturing the host cell of claim 9 under conditions for protein expression; and
    b) recovering the protein from the host cell culture.

11. A transgenic cell line or organism comprising the vector of claim 8.

12. A method of using a cDNA to screen a plurality of molecules or compounds, the method comprising:
    a) combining the cDNA of claim 1 with a plurality of molecules or compounds under conditions to allow specific binding; and
    b) detecting specific binding, thereby identifying a molecule or compound which specifically binds the cDNA.

13. The method of claim 12 wherein the molecules or compounds are selected from aptamers, DNA molecules, RNA molecules, peptide nucleic acids, artificial chromosome constructions, peptides, transcription factors, enhancers, repressors, and regulatory molecules.

14. An isolated cDNA comprising a polynucleotide selected from:
    a) a polynucleotide having a nucleic acid sequence of SEQ ID NO:2;
    b) a polynucleotide having a nucleic acid sequence selected from SEQ ID NOs:3–9, 11 and 12; and
    c) a complement of a)–b).

* * * * *